US008119766B2

(12) United States Patent
Campbell et al.

(10) Patent No.: US 8,119,766 B2
(45) Date of Patent: Feb. 21, 2012

(54) INCREASING FUNCTIONAL GLYCOSYLATION OF ALPHA-DYSTROGLYCAN IN THE TREATMENT OF MUSCLE DEGENERATION

(75) Inventors: Kevin P. Campbell, Iowa City, IA (US); Rita Barresi, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 168 days.

(21) Appl. No.: 11/143,885

(22) Filed: Jun. 2, 2005

(65) Prior Publication Data

US 2006/0276376 A1    Dec. 7, 2006

(51) Int. Cl.
*C07K 1/00*     (2006.01)
*C07H 21/02*    (2006.01)
*C07H 21/04*    (2006.01)
*A61K 48/00*    (2006.01)

(52) U.S. Cl. .................. 530/350; 536/23.1; 514/44
(58) Field of Classification Search ............... 514/44
See application file for complete search history.

(56) References Cited

OTHER PUBLICATIONS

Muntoni et al. (Jul. 2004) Nat. Med. 10:676-677.*
Chamberlin JS (2002) H. Mol. Gen. 11:2355-2362.*
Pfeifer and Verma (2001) Annu. Rev. Genomics. Hum. Genet. 2:177-211.*
Johnson-Saliba et al. (2001) Curr. Drug. Targets 2:371-99.*
Shoji et al. (2004) Current Pharmaceutical Design 10 :785-796.*
Barresi et al. (Jun. 6, 2004) Nat. Med. 10 :696-703.*
Nguyen et al. (2002) PNAS 99 :5616-5621.*
Dictionary.com Unabridged (v 1.1) [online], 2006 [retrieved on Jan. 10, 2007]. Retrieved from the Internet:< URL: http://dictionary.reference.com/browse/in%20situ, pp. 1-4.*
Muntoni et al., 2004, Nature Medicine, 10: 676-677.*
Montanaro and Carbonetto, 2003, Neuron, 37: 193-196.*
Martin and Freeze, 2003, Glycobiology, 13: 67R-75R.*
Begley, 2004, Pharmacology and Therapeutics, 104: 29-45.*
Adessi and Soto, 2002, Current Medicinal Chemistry, 9: 963-978.*
Atkinson and Leiter, 1999, Nature Medicine, 5: 601-604.*
Lowenstein and Castro, 2004, Current Opinion in Pharmacology, 4: 91-97.*
Verma and Weitzman, 2005, Annual Review in Biochemistry, 74: 711-738.*
Abdallah, et al., 1995, Biol. Cell., 85: 1-7.*
Diaz et al., 1998, Journal of Virology, 72: 789-795.*
Bartke et al., 2002, Neuropeptides, 36: 201-208.*
Hammer et al., 1986, J. of Anim. Sci., 63: 269-278.*
Fenske et al., 2001, Current Opinion in Molecular Therapeutics, 3: 153-158.*
Gardlik et al., 2005, Med. Sci. Monit. 11: RA110-RA121.*
Romero et al., 2004, Human Gene Therapy, 15: 1065-1076.*
Barresi and Campbell, 2005, Journal of Cell Science, 119, 199-207.*
Schachter et al., 2004, Glycoconjugate Journal, 20: 291-300.*
Endo and Toda, 2003, Biol. Pharm. Bull, 26: 1641-1647.*
Longman, et al., 2003, Human Molecular Genetics, 12: 2853-2861.*

(Continued)

*Primary Examiner* — Joanne Hama
(74) *Attorney, Agent, or Firm* — Pierce Atwood, LLP; Kevin M. Farrell, Esq.; David J. Wison, Esq.

(57) ABSTRACT

Disclosed is a method for the prevention and/or treatment of muscle degeneration. In this method, a subject recognized as having muscle degeneration is treated with a composition effective to increase functional glycosylation of α-dystroglycan in an affected tissue in the subject. Functional glycosylation is to be increased to an extent wherein the binding of α-dystroglycan to its ligands in the affected tissue is rescued to levels substantially similar to those in an evenly matched tissue unaffected by degeneration. One effective means for increasing functional glycosylation of α-dystroglycan in a subject includes increasing glycosyltransferase activity, such as LARGE or LARGE2 activity, in the muscle of the subject. Therapeutic glycosylated peptide compositions are also provided.

12 Claims, 17 Drawing Sheets
(11 of 17 Drawing Sheet(s) Filed in Color)

OTHER PUBLICATIONS

Barresi et al., 2004, Nature Medicine, 10: 696-703.*
Vachon et al., 1996, The Journal of Cell Biology, 134: 1483-1497.*
Willer et al., 2003, Current Opinion in Structural Biology, 13: 621-630.*
Martin-Rendon et al., 2003, Trends in Pharmacological Sciences, 24: 178-183.*
Huang et al., 2000, Gene Therapy, 7: 314-320.*

* cited by examiner 316-340  ATPTPVTAIGPPTTAIQEPPSRIVP 338-361  IVPTPTSPAIAPPTETMAPPVRDP 362-408  VPGKPTVTIRTRGAIIQTPTLGPIQ
PTRVSEAGTTVPGQIRPTLTIP

TPT-$X_{3-4}$-I-$X_{1-2}$-PT

Large acceptor motif

FIG. 16

| construct | template | primers |
|---|---|---|
| 316-340 | DGFc5pcDNA3 | T7 x 340R |
| 316-361 | DGFc5pcDNA3 | T7 x 361R |
| 338-361 | 338-408 | T7 x 361R |
| 362-408 | 362-485 | T7 x 408R |

Primers used for mutants

340R: TTTGATCAGGCACGATCCTGGACGGCGG
361R: TTTGATCAGGATCCCTGACTGGAGGAGC
315R: TTCACGTGGATCTGCCTTCGGATACGC
338F: AATCGCGAATCGTGCCTACCCCACTTCT
408R: TTTGATCAGGAATGGTCACCGTTGCACG
362.485R: CCGTGGGCTTCCCAGGAACAGGGGCATGGATCTGCCTTCGGATAC
362.485F: GTATCCGAAGGCAGATCCATGCCCCTGTTCCTGGGAAGCCCACGG
485R: TTTGATCACTGGTGGTGCGGATACGA
409.485R: CTGCTGTGGGCTCCACGTAGCCGGCATGGATCTGCCTTCGGATAC
409.485F: GTATCCGAAGGCAGATCCATGCCGGCTACGTGGAGCCCACAGCAG

FIG. 17

INCREASING FUNCTIONAL GLYCOSYLATION OF ALPHA-DYSTROGLYCAN IN THE TREATMENT OF MUSCLE DEGENERATION

BACKGROUND OF THE INVENTION

Muscular dystrophies are a diverse group of inherited disorders characterized by progressive muscle weakness and wasting (Bushby 2000; Cohn and Campbell, 2001). Duchenne muscular dystrophy (DMD) is the most common form of childhood muscular dystrophy and is caused by mutations in the dystrophin gene that lead to the complete absence of dystrophin in skeletal and cardiac muscle.

Efforts to identify the function of dystrophin have lead to the identification and characterization of the dystrophin-glycoprotein complex (DGC) in skeletal muscle. The DGC is a multimeric transmembrane protein complex in the sarcolemma. The proteins that comprise the DGC are the cytoplasmic proteins dystrophin, dystrobrevin and the syntrophins, and the sarcolemmal localized dystroglycans ($\alpha$ and $\beta$ subunits), sarcoglycans ($\alpha$, $\beta$, $\gamma$ and $\delta$ subunits), and sarcospan (Campbell, 1995; Crosbie et al., 1997; Yang et al., 1994). Dystroglycan (DG) is a key component of the DGC (Ervasti et al., 1991) that is composed of $\alpha$- and $\beta$-subunits which are post-translationally derived from a single mRNA encoded by the DAG1 gene (Ibraghimov-Beskrovnaya et al., 1992). In skeletal muscle $\alpha$-dystroglycan is a highly glycosylated peripheral membrane protein that binds laminin-2 in the extracellular matrix, whereas $\beta$-dystroglycan is an integral membrane glycoprotein that anchors $\alpha$-dystroglycan to the membrane and binds dystrophin intracellularly. Accumulated evidence indicates that the DGC provides a stable structural link between the actin cytoskeleton and the extracellular matrix in order to maintain the integrity of the muscle cell membrane during cycles of contraction and relaxation. The importance of the DGC in normal muscle function is underscored by discoveries that mutations in several components of the DGC give rise to distinct muscular dystrophies.

To date, there are no reports indicating that dystroglycan mutations cause muscular dystrophy in humans. However, dystroglycan structure and function are perturbed in many types of muscular dystrophy (Ibraghimov-Beskrovnaya et al., 1992; Duclos et al., 1998; Coral-Vazquez et al., 1999; Allamand et al., 2002). $\alpha$-Dystroglycan is greatly reduced from the sarcolemma in muscle from patients with Duchenne muscular dystrophy and from the mdx mouse model. In limb-girdle muscular dystrophy (LGMD) patients, $\alpha$- and $\beta$-dystroglycan are localized to the sarcolemma but $\alpha$-dystroglycan is not appropriately anchored to the muscle plasma membrane. In both cases, perturbation of the dystroglycan complex results in a break in the structural connection between the sarcolemma and extracellular matrix.

Recently, a series of additional muscular dystrophies, dystroglycanopathies, have been identified. Emerging genetic data show that these diseases are linked to mutations in genes with homology to glycosyltransferases, enzymes that add or modify sugar structures on proteins. These diseases are typically characterized by severe muscular dystrophy including muscle necrosis and regeneration; some also exhibit a brain phenotype with neuronal migration defects as well as eye abnormalities and variable heart involvement. Fukuyama congenital muscular dystrophy (FCMD), muscle-eye-brain disease (MEB), Walker-Warburg syndrome (WWS), LGMD2I, MDC1C, and MDC1D are all dystroglycanopathies. The fukutin gene in Fukuyama congenital muscular dystrophy was the first to be identified and encodes a protein with homology to glycoconjugate modifying enzymes (Kobayashi et al., 1998). Actual glycosyltransferase activity has been demonstrated for proteins mutated in muscle-eye-brain disease and Walker-Warburg syndrome, the O-mannosyl-$\beta$1, 2-N-acetylglucosaminyltransferase (POMGnT1) and Protein O-mannosyltransferase 1 and 2 (POMT1 and 2), respectively (Yoshida et al., 2001; Beltran-Valero de Bernabe. et al., 2002; Zhang et al., 2002; Manya et al., 2004; van Reeuwijk et al., 2005). LARGE, the gene mutated in Large-$^{myd}$ mice and MDC1D patients, encodes for a putative glycosyltransferase with two structurally distinct domains homologous to bacterial $\alpha$-glycosyltransferase and mammalian $\beta$-1, 3-N-acetylglucosaminyltransferase (Peyrard et al., 1999; Grewal et al., 2001; Longman et al., 2003). Biochemical analysis of muscle biopsies has revealed a convergent role for these proteins in the glycosylation of $\alpha$-dystroglycan, a process required for functional activity of this protein. The abnormal glycosylation of dystroglycan in disease disrupts the normal binding activity for each of its major extracellular matrix ligands in muscle and brain. Thus, disruption of dystroglycan ligand binding resulting in a loss of the functional link between the cytoskeleton and the extracellular matrix leads to severe muscular dystrophy (Michele et al., 2002).

SUMMARY OF THE INVENTION

The present invention relates to a method for preventing or treating muscle degeneration. In this method, a subject recognized as having muscle degeneration is treated with a composition effective to increase functional glycosylation of $\alpha$-dystroglycan in an affected tissue in the subject. In this method, the functional glycosylation is to be increased to an extent wherein the binding of $\alpha$-dystroglycan to its ligands—particularly laminin-1, laminin-2, laminin-10/11, perlecan, agrin, and/or neurexin—in the affected tissue is rescued to levels substantially similar to or higher than those in an evenly matched tissue unaffected by degeneration.

One effective means for increasing functional glycosylation of $\alpha$-dystroglycan in a subject includes increasing glycosyltransferase activity in the muscle of the subject. The glycosyltransferase may be any glycosyltransferase that increases functional glycosylation of $\alpha$-dystroglycan in the affected muscle of a subject. In a preferred embodiment the glycosyltransferase activity is LARGE or LARGE2 activity. Glycosyltransferases other than LARGE may be identified and used in the methods of the present invention.

A composition effective to increase functional glycosylation of $\alpha$-dystroglycan may be introduced into a muscle cell or tissue by various means in the methods of the present invention. A cell may be contacted directly with a composition such as LARGE or LARGE2, or a biologically active fragment thereof, under physiological conditions. Means for administration of the composition include but are not limited to direct injection. Alternatively, a muscle cell may express an exogenous product such as LARGE or LARGE2 from an introduced exogenous construct harboring an expressible cDNA construct or constructs. In animals or individuals, the construct may be delivered by methods of gene therapy, which are known in the art. The composition may further be introduced indirectly by increasing the expression of an endogenous glycosyltransferase gene such as LARGE or LARGE2. Alternatively, expressible RNA may be delivered to muscle by injection or other delivery means already known in the art.

A subject to be treated with a method of the present invention may be asymptomatic or symptomatic. Wherein the muscle degeneration is symptomatic the muscle degeneration may, for example, be due to an age-related or injury-related weakness or to muscle atrophy. The muscle degeneration may also be due to a manifestation of disease state such as congenital muscular dystrophy. Examples of congenital muscular dystrophies to be treated in conjunction with the present invention include Fukuyama congenital muscular dystrophy, muscle-eye-brain disease, Walker-Warburg syndrome, Duchenne muscular dystrophy, Becker muscular dystrophy, and limb-girdle muscular dystrophy. Wherein the subject is asymptomatic, the subject may not be afflicted with congenital muscular dystrophy, but may merely be genetically predisposed to acquiring the disease. Wherein the degeneration or predisposition to the degeneration is due to a disease state such as congenital muscular dystrophy, a subject may be screened for the presence, absence, or change in any of the genes, or gene products thereof, implicated in any of the various forms of the disease, wherein the presence, absence, or change results in a manifestation of or predisposition to a disease state for that muscular dystrophy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 16 depicts the amino acid sequences of the three independent regions modified by LARGE, 316-340 (SEQ ID NO: 1), 338-361 (SEQ ID NO: 2), and 362-408 SEQ ID NO: 3). The acceptor motif is also shown (SEQ ID NO: 4).

FIG. 17 depicts the sequences used in constructing the -DG deletion mutants used in Example 3 (SEQ ID NOS: 5-14, respectively, in order of appearance).

DETAILED DESCRIPTION OF THE INVENTION

Figure 1:
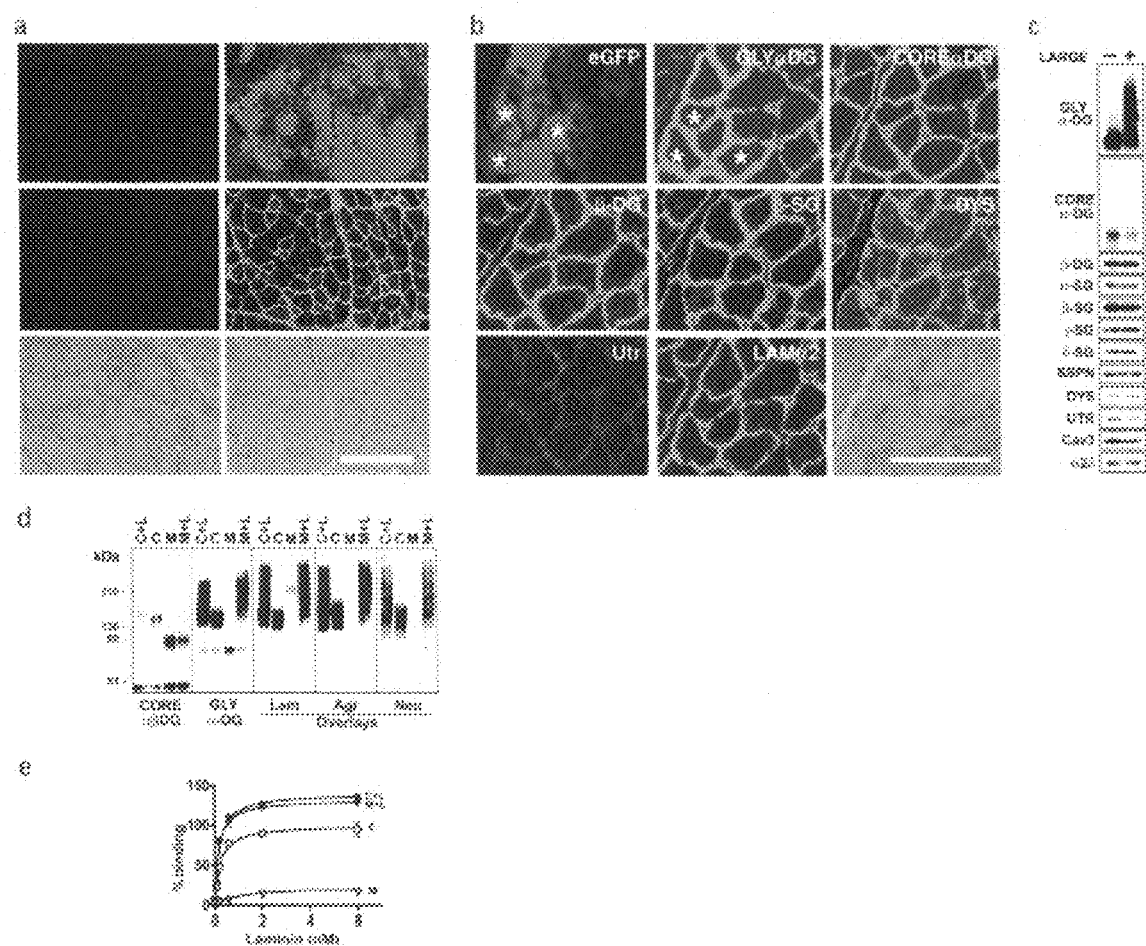
FIG. 1 shows that expression of LARGE generates heavily glycosylated α-DG. (a) Hematoxylin-eosin staining and fluorescence localization of eGFP and glycosylated α-DG in Large$^{myd}$ cryosections of quadriceps muscles after injection of Ad5-LARGE/eGFP (right). Contralateral untreated muscles are also shown (left). Scale bar 100 µm. (b) Analysis of wild type skeletal muscle treated with Ad5-LARGE/eGFP. Hematoxylin-eosin staining and fluorescence localization of eGFP, glycosylated α-DG (GLYα-DG), α-DG core peptide (COREα-DG), β-DG, laminin α2 (Lamα2), β-sarcoglycan (β-SG), dystrophin (DYS), and utrophin (Utr). Asterisks indicate three transduced fibers. Scale bar 100 µm. (c) SDS-PAGE of KCl-washed membranes from control skeletal muscle. Immunoblots performed with antibodies to glycosylated α-DG (GLYα-DG), α-DG core peptide (COREα-DG), β-DG, sarcoglycans (α-SG, β-SG, γ-SG, δ-SG), sarcospan (SSPN), dystrophin (DYS), utrophin (Utr), and caveolin-3 (Cav-3). An antibody to the $Ca^{2+}$ channel subunit α2δ was used as a loading control. (d) SDS-PAGE analysis of WGA-enriched homogenates from control and Large$^{myd}$ untreated (C, M), and treated with Ad5-LARGE/eGFP (C+L, M+L) using antibodies to dystroglycan core protein (CORE-αβDG) and glycosylated α-DG (GLYα-DG). Bands at ~70 kDa in GLYα-DG panel represent endogenous immunoglobulins. Ligand overlay assays with laminin (Lam), agrin (Agr), and neurexin (Neu). (e) Solid-phase laminin-binding activity of α-DG from treated (C+L, M+L) and untreated (C, M) control and Large$^{myd}$ skeletal muscle.

The present invention is based on the finding that LARGE expression can prevent muscle degeneration in various types of muscular dystrophy. More specifically, experiments in the Exemplification section that follows demonstrate that overexpression of LARGE in a mouse model for congenital muscular dystrophy ameliorates the muscle phenotype of the disease. Overexpression of LARGE in skeletal muscle induces synthesis of functional, highly glycosylated α-dystroglycan that not only displays increased affinity for its extracellular ligands but also restores α-dystroglycan receptor function in Large$^{myd}$ mice. Notably, LARGE circumvents the α-dystroglycan defect in cells from individuals with genetically distinct types of congenital muscular dystrophy. In fact, increased LARGE activity rescues the cytoskeleton-extracellular matrix link in cells from individuals with Fukuyama congenital muscular dystrophy (FCMD) and Walker-Warburg syndrome (WWS), whereby glycan-enriched α-dystroglycan coordinates the organization of laminin on the cell surface. The present invention provides the first evidence that disruption of dystroglycan-laminin linkage, through the absence of glycosylation or LARGE recognition, is central to muscle cell degeneration in muscular dystrophy. The findings presented herein represent the first evidence that LARGE expression can prevent muscle degeneration in multiple types of muscular dystrophy and further suggest novel therapeutic methods for the prevention and/or treatment of various forms of muscular dystrophies.

The findings provided herein indicate that increasing the glycosylation state of α-dystroglycan can improve muscle phenotype. Overexpression of LARGE as demonstrated restored α-dystroglycan function in cell lines derived from individuals bearing defects in a variety of glycosyltransferases, not simply defects in LARGE. Unexpectedly, the effect of LARGE was similar in a variety of cell types and tissues, suggesting that the induction of LARGE may be effective in the treatment not only of MDC1D but also of FCMD, MEB, WWS, LGMD2I and other glycosyltransferase-deficient muscular dystrophies. The finding that an endogenous protein can modulate the glycosylation of α-dystroglycan in genetically distinct diseases without undesirable effects arising from its upregulation makes LARGE and related genes such as LARGE2 particularly attractive targets for the design of therapies to manipulate α-dystroglycan glycosylation. Glycotherapies and treatments aimed at modulating the expression or the activity of LARGE or LARGE2 may be the basis of therapy for the whole group of glycosyltransferase-deficient muscular dystrophies. Several reported muscle-only pathologies associated with defective glycosylation of α-dystroglycan and unlinked to known genes might particularly benefit from such therapeutic approaches.

Because LARGE restored α-dystroglycan function in cell lines derived from individuals with defects in other known glycosyltransferases, the present findings suggest that increasing α-dystroglycan glycosylation in general may be useful in treating a wide range of congenital muscular dystrophies. Glycotherapies and treatments not specifically related to the use of LARGE may therefore be used for increasing the functional glycosylation of α-dystroglycan for treating muscle degeneration.

The present invention relates to a method for preventing or treating muscle degeneration. In this method, a subject recognized as having muscle degeneration is treated with a composition effective to increase functional glycosylation of α-dystroglycan in an affected tissue in the subject. In this method, the functional glycosylation is to be increased to an extent wherein the binding of α-dystroglycan to its ligands—particularly laminin-1, laminin-2, laminin-10/11, perlecan, agrin, and/or neurexin—in the affected tissue is rescued to levels substantially similar to or higher than those in an evenly matched tissue unaffected by degeneration.

Diagnosis of a subject in need of treatment for muscle degeneration is to be determined by any of various means as is known in the art. A subject to be treated in conjunction with the present invention may be symptomatic or asymptomatic. Wherein the muscle degeneration is symptomatic the degeneration may be diagnosed by consultation with a qualified clinician. The muscle degeneration may, for example, be due to an age-related or injury-related weakness or to muscle atrophy and not require any laboratory tests for accurate diagnosis. Wherein the subject is asymptomatic, the subject may not be afflicted with congenital muscular dystrophy, but may merely be genetically predisposed to acquiring the disease. Wherein the degeneration or predisposition to the degeneration is due to a disease state such as congenital muscular dystrophy, a subject may be screened for the presence, absence, or change in any of the genes, or gene products thereof, implicated in any of the various forms of the disease, wherein the presence, absence, or change results in a manifestation of or predisposition to a disease state for that muscular dystrophy. Screening may include genetic or biochemical testing of any such gene or gene product in the subject. Assessment of functional dystrophin, for example, in muscle biopsy tissue may be used to diagnose Duchenne or Becker muscular dystrophy, as is known in the art. Assessment of functional sarcoglycan may also, for example, be used for the diagnosis of limb-girdle muscular dystrophy. Histological features of biopsy tissue may also be considered during screening. Typical histological features of skeletal muscle characteristic to muscular dystrophy include central nucleation, myofibrosis, and necrosis of muscle fibers, and also loss of the sarcoglycan complex coupled with the reduction of dystroglycan, sarcospan, and dystrophin from the sarcolemma. Examination or screening in the context of the present invention includes prenatal screening.

Screening for aberrant gene products that may be characteristic of congenital muscular dystrophy may be achieved by various means as known in the art. Mutations that cause a change in expression levels in key genes, such as mutations in transcriptional or translational regulatory elements, may be detected from tissue biopsy and subsequent testing with, for example, immunodiagnostics. Mutations that cause a change in protein size, such as missense, frame-shift, or destabilizing mutations, may be detected in the same manner. The use of nucleic acid probes for diagnosing autosomal recessive limb-girdle muscular dystrophy is described in U.S. Pat. Nos. 5,672,694 and 6,211,340 both to Campbell et al., the contents of which are herein incorporated by reference. The use of antibodies for diagnosing autosomal recessive muscular dystrophy is described in U.S. Pat. No. 5,308,752 to Campbell et al., the contents of which are herein incorporated by reference. The use of antibodies to detect the absence or reduction of a particular non-dystrophin component of the dystroglycan-glycoprotein complex for diagnosing Fukuyama congenital muscular dystrophy and Duchenne-type muscular dystrophy is described U.S. Pat. No. 5,260,209 to Campbell et al., the contents of which are herein incorporated by reference.

Such mutations can also be identified through sequence analysis of genetic material, by either direct sequencing, or hybridization with specific nucleic acid probes. Such diagnostic methods are performed by isolating nucleic acids, either genomic DNA, cDNA or mRNA, from an individual and testing the diagnostic probes for the ability to hybridize to the isolated nucleic acid. When necessary, the nucleic acid sequence can be amplified by the PCR prior to hybridization analysis. A working example of this technique uses specific oligonucleotides designed to hybridize to specific mutations in the β-sarcoglycan gene (Campbell et al., (1997) U.S. Pat. No. 5,672,694). As more mutations in genes are identified as contributing to LGMD and other congenital muscular dystrophies, similar oligo probes can be designed and used for rapid diagnostic analysis. In lieu of the development of specific oligo probes, mutations can be identified by sequence analysis of such individual genes. The genetic material of the individual genes can be sequenced, and mutations that would adversely effect expression or structure of the corresponding protein can be identified by comparison to wild type sequences. Detection of severe childhood autosomal recessive muscular dystrophies by direct sequencing methods is described in U.S. Pat. Nos. 5,733,732; 5,672,694; and 6,211,340, all to Campbell et al., the contents of which are herein incorporated by reference. cDNA or mRNA specific for individual genes implicated in congenital muscular dystrophy such as α, β, γ, or δ sarcoglycan genes can be examined quantitatively for reduction in transcript levels, and also for detectable size differences indicative of frame shift or missense mutations by the techniques of DNA or RNA hybridization analysis, or by amplification using the polymerase chain reaction (PCR).

Mutations in various genes have been identified and reported as contributing to various forms of congenital muscular dystrophy. Several mutations in the various sarcoglycan genes have been implicated in the onset of limb-girdle muscular dystrophy Piccolo et al., Nat. Genet. 10, 243-245 (1995); Piccolo et al., J Med Genet. 34, 470-475 (1997); Duggan, et al., Neurogenetics 1, 827-834 (1997); Duggan et al., N Engl J Med. 336, 618-624 (1997); Carrier et al., J Med Genet. 34, 470-475 (1997).

Because increasing the glycosylation of α-dystroglycan may be effective in treating a variety of diseases characterized by muscular degeneration, correlation of muscle weakness with a specific disease, although desirable, is not necessary. Treatment may be given to a subject upon diagnosis of muscle weakness. Knowledge of the specific cause of the muscle weakness is not a requirement. As shown in the Exemplification section below, increasing the functional glycosylation state of α-dystroglycan in genetically distinct diseases was achieved through the use of LARGE upregulation without apparent undesirable side effects.

Once the need for treatment has been established through an appropriate diagnosis, a composition effective to increase glycosylation of α-dystroglycan is to be introduced into the affected muscle tissue of the subject. Administration of the composition may be achieved via any of a number of ways as described below. As new methods for administering such compounds to muscle tissue become available, these may also be used in conjunction with the present invention.

One effective means for increasing functional glycosylation of α-dystroglycan in a subject includes increasing glycosyltransferase activity in the muscle of the subject. The glycosyltransferase may be any glycosyltransferase that increases functional glycosylation of α-dystroglycan in the affected muscle of a subject. In a preferred embodiment the glycosyltransferase activity is LARGE or LARGE2 activity. Glycosyltransferases other than LARGE or LARGE2 may be identified by the methods provided in the Exemplification section that follows. As an example, a putative glycosyltransferase may be introduced into myoblasts or fibroblasts from subjects with a congenital muscular dystrophy such as FCMD. The expression and biochemical characteristics of α-dystroglycan in such experimental cells may be compared to that of control cells in which the putative glycosyltransferase has not been introduced. Expression of glycosylated α-dystroglycan may be detected by immunofluorescence analysis and compared in control vs. experimental cells. Immunoblotting with antibodies to α-dystroglycan core peptide may be used to assay for a specific glycosylation state, with the specific molecular weight being indicative of a glycosylation state. Functional glycosylation may be determined by assaying binding of α-dystroglycan to its ligands. As an example, a gain in laminin, agrin, and neurexin binding in the experimental cells as compared to control cells is an indicator that functional glycosylation has been increased. Increased expression of functionally glycosylated α-dystroglycan in the experimental cells as compared to the control cells is indicative that the putative glycosyltransferase is likely to be effective in preventing or treating muscle cell degeneration.

A method for preventing or treating muscle degeneration may include introducing into a muscle tissue or cell a composition containing a full-length amino acid sequence such as LARGE under conditions effective to increase glycosylation of α-dystroglycan in the subject. One of skill in the art will recognize that a biologically active fragment such as that of LARGE or LARGE2 may be used in lieu of the full-length amino acid sequence in the context of the present invention. A "biologically active fragment" is intended to encompass any mimetic, truncation, deletion, and/or substitution of full-length LARGE or LARGE2 with the ability to increase functional glycosylation of α-dystroglycan in the methods of the present invention. A biologically active fragment may further be a protein, polypeptide, or peptide.

One of skill in the art will recognize that a composition effective to increase functional glycosylation of α-dystroglycan may be introduced into a muscle cell or tissue by various means in the methods of the present invention. A cell may be contacted directly with a composition such as LARGE or LARGE2, or a biologically active fragment thereof, under physiological conditions. Means for administration of the composition include but are not limited to direct injection. Alternatively, a muscle cell may express an exogenous product such as LARGE or LARGE2 from an introduced exogenous construct harboring an expressible cDNA construct or constructs. In animals or individuals, the construct may be delivered by methods of gene therapy, which are known in the art. The composition may further be introduced indirectly by increasing the expression of an endogenous glycosyltransferase gene such as LARGE. Alternatively, expressible RNA may be delivered to muscle by injection or other delivery means already known in the art. LARGE and LARGE2 DNA, RNA, and amino acid sequences are known in the art (see for example, Peyrard et al. (1999), *PNAS* 96: 598-603 and Fujimura et al. (2005) *Biochem Biophys Res Commun.* 329 (3):1162-71, the contents of both which are herein incorporated by reference). One of skill in the art will recognize that sequences substantially similar to LARGE or LARGE2 may be employed in the context of the present invention. For example, LARGE or LARGE2 sequences containing fusions, point mutations, truncations, and/or deletions may also be employed, provided that a fusion, point mutation, truncation, and/or deletion does not abolish LARGE or LARGE2 activity.

An appropriate expression vector may be used to deliver exogenous nucleic acid to a recipient muscle cell in the methods of the invention. In order to achieve effective gene therapy, the expression vector must be designed for efficient cell uptake and gene product expression. Use of adenovirus or adeno-associated virus (AAV) based vectors for gene delivery have been described (Berkner, K. L., Current Topics in Microbiol. and Imunol. 158, 39-66 (1992); Stratford-Perricaudet et al., Hum. Gene Ther. 1, 241-256 (1990); Rosenfeld et al. Cell 8, 143-144 (1992); Stratford-Perricaudet et al. J. Clin. Invest. 90, 626-630 (1992)). Specific methods for gene therapy useful in the context of the present invention depend largely upon the expression system employed; however, most involve insertion of coding sequence at an appropriate position within the expression vector, and subsequent delivery of the expression vector to the target muscle tissue for expression.

In the methods of the present invention, the composition may be administered to an animal or individual in a physiologically acceptable carrier in a therapeutically effective amount. Said compound or compounds may be administered alone or in combination with other therapies and may be delivered intravenously, intramuscularly, subcutaneously, or orally to a subject. The subject may be an animal, and may further be a human or dog. Administration may be local, although systemic administration may be preferable.

In another embodiment, the present invention relates to therapeutic glycosylated peptide compositions. The peptides are deletion mutants of α-dystroglycan that have been glycosylated in vitro. A peptide of the present invention is short enough in sequence to be used as a therapeutic for the treatment of muscle degeneration.

While specific embodiments of the present invention have been described, it will be apparent to those skilled in the art that various modifications thereto can be made without departing from the spirit and scope of the invention as defined in the examples and appended claims.

EXEMPLIFICATION

Example 1

LARGE can Functionally Bypass α-dystroglycan Glycosylation Defects in Distinct Congenital Muscular Dystrophies Results LARGE prevents muscular dystrophy in Large$^{myd}$ mice. To investigate the effect of LARGE on α-DG glycosylation, we generated an adenovirus expressing LARGE and eGFP (Ad5-LARGE/eGFP). Gene transfer was performed in Large$^{myd}$ and littermate pups. Injected and non-injected contralateral leg muscles were examined for DG expression using a panel of antibodies to core and glycosylated α-DG. Transduction efficiency estimated by eGFP expression was 40-80% (FIG. 1a). All transduced muscle fibers reacted with antibodies to glycosylated α-DG. Expression of other DGC components did not change (FIG. 1b, and not shown). Dystrophic histological features such as internally placed nuclei were reduced by over 70% in Large$^{myd}$ transduced muscles and significant reduction in fiber size variation was observed after treatment (P=0.007). Analysis of Large$^{myd}$ mice treated with Ad5-LARGE/eGFP at older ages (12 days to 5 weeks) did not lead to conclusive results due to inflammatory response to the virus and rapid loss of expression of eGFP and glycosylated α-DG. Importantly, LARGE gene transfer in healthy muscle did not cause histological abnormalities (FIG. 1b). Unexpectedly, we detected stronger expression of α-DG glyco-epitopes at the sarcolemma of transduced control fibers, suggesting that LARGE gene transfer leads to the synthesis of α-DG species more enriched in glycans (FIG. 1b). Indeed, immunoblots of KCl-washed membranes from control skeletal muscle revealed no changes in the DGC after treatment with Ad5-LARGE/eGFP except for more heavily glycosylated α-DG (FIG. 1c). Immunoblot analysis of wheat germ agglutinin (WGA)-enriched fractions from treated control and Large$^{myd}$ muscles showed glycosylated α-DG as a broad band of relative molecular mass ($M_r$) 150-300 kDa (FIG. 1d). Core peptide antibodies poorly recognized high $M_r$ α-DG likely due to masking of the epitope by the additional carbohydrate moieties. Residual hypoglycosylated α-DG (90 kDa) from non-transduced fibers was also detected in Large$^{myd}$ treated muscle (Michele et al., Nature 418 (6896): 417-22 (2002)). Ligand overlay assays displayed rescue of α-DG receptor function in treated Large$^{myd}$ muscle, and persistent ligand binding activity of heavily glycosylated α-DG (FIG. 1d). Quantitative solid-phase laminin-binding assays of WGA-enriched fractions revealed enhanced activity of non-denatured α-DG in Large$^{myd}$ and control muscles after viral transduction (FIG. 1e). We obtained similar results in analogous experiments performed on primary myoblasts cultures from control and Large$^{myd}$ mice. Interestingly, forced expression of LARGE induced synthesis of glycosylated α-DG in all transduced cell types—myotubes, myoblasts and fibroblasts (not shown).

In order to demonstrate functional benefit conferred by LARGE gene transfer, we exercised Large$^{myd}$ mice and control littermates injected with Ad5-LARGE/eGFP in hamstring muscles, where the transduction efficacy was higher. EBD uptake revealed that skeletal muscles of Large$^{myd}$ mice were susceptible to exercise-induced sarcolemmal injury. Quantitative image analysis indicated that EBD uptake in Large$^{myd}$ muscles decreased on average from 11.3% to 1.4% upon LARGE gene transfer. We never observed EBD uptake in transduced areas of Large$^{myd}$ muscle and in control skeletal muscle, thus demonstrating improved functional features of corrected muscles and absence of undesirable consequences of overexpression of LARGE.

Figure 2:
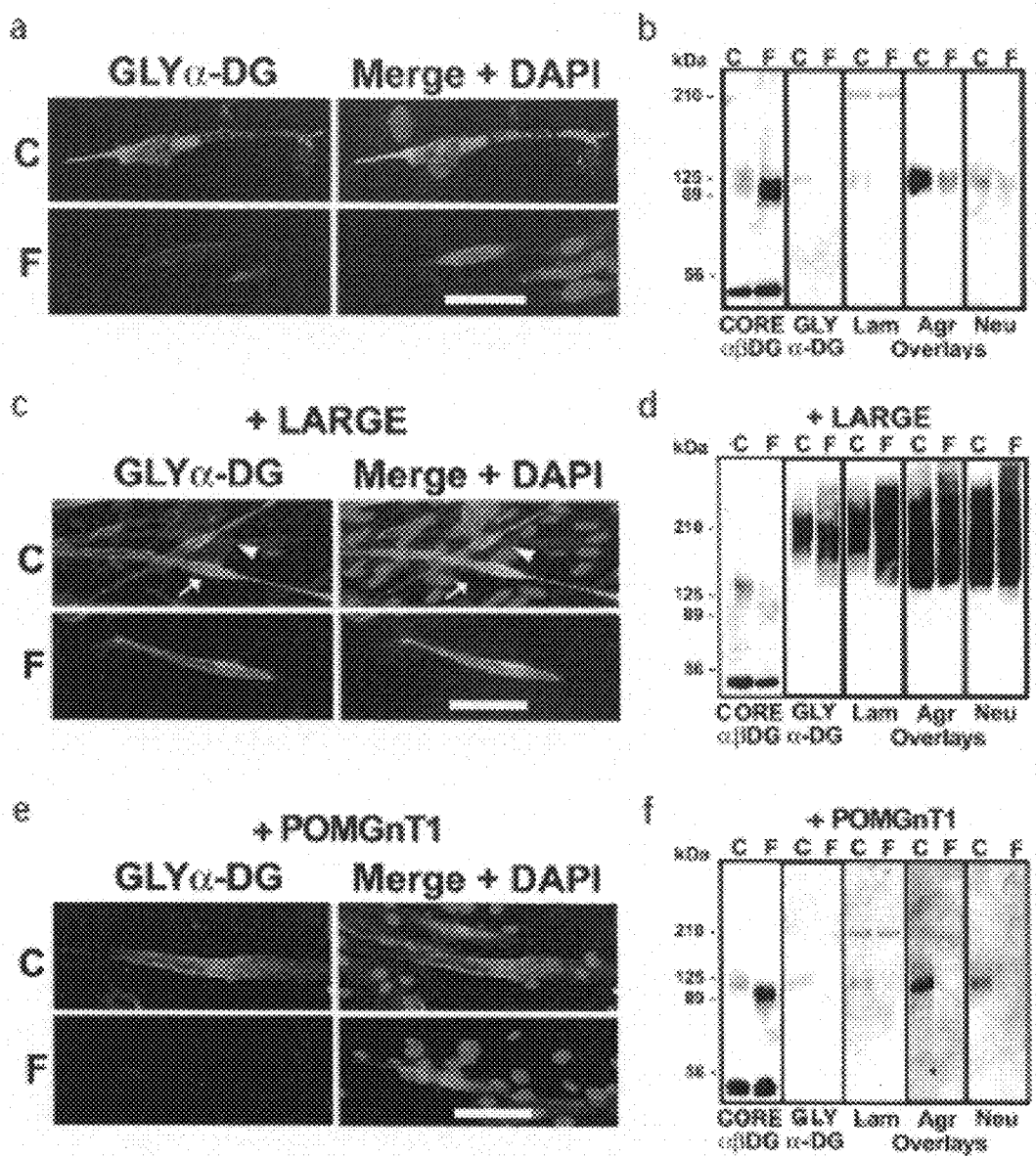
FIG. 2 illustrates that LARGE generates functional α-DG in FCMD myoblasts. Localization of desmin (a), eGFP (c, e), glycosylated α-DG (GLYα-DG), and nuclear labelling (DAPI) in control (C) and FCMD (F) cultures untreated (a) and treated with Ad5-LARGE/eGFP (c) or Ad5-POMGnT1/eGFP (e). Arrows indicate myotubes, arrowheads indicate myoblasts. Scale bars 10 µm. SDS-PAGE of WGA-enriched lysates from control (C) and FCMD (F) myoblasts untreated (b) and infected with Ad5-LARGE/eGFP (d) or Ad5-POMGnT1/eGFP (f). Immunoblots with antibodies to dystroglycan core protein (CORE-αβDG) and glycosylated α-DG (GLYα-DG). Laminin (Lam), neurexin (Neu), and agrin (Agr) were used for ligand overlay assays. Bands at ~210 kDa in b and f represent endogenous laminin. Data shown are representative of three patients.

LARGE generates functional α-DG in FCMD myoblasts. Our findings in control and Large$^{myd}$ muscle suggest that LARGE is a critical component of the glycosylation machinery of α-DG. Genetic and biochemical analysis of dystroglycanopathy patients indicates that residual glycosylation activity is present (Kondo-Iida et al., Human Molecular Genetics 8(12): 2303-9 (1999); Michele et al., Nature 418(6896): 417-22 (2002)). Thus, we investigated whether the residual activity could be modulated or enhanced by LARGE expression in congenital muscular dystrophy patients' cells. We first examined the expression and biochemical characteristics of α-DG in myoblasts obtained from three FCMD patients and one control patient. The expression of functionally glycosylated α-DG increased throughout the differentiation of control myoblasts into myotubes; in contrast, highly reduced and patchy expression of glycosylated α-DG was observed in FCMD cultures (FIG. 2a), indicating significant reduction of fukutin activity in FCMD cells. Immunoblot analysis of WGA-enriched cell lysates with antibodies to DG core peptide revealed a smaller developmental α-DG isoform of 110-125 kDa in control myoblasts that exhibited binding activity for laminin, neurexin, and agrin (FIG. 2b). In FCMD myoblasts, α-DG was identified as a broad band of 90-125 kDa with anti-core DG antibodies, demonstrating the expression of variably glycosylated α-DG species (FIG. 2b). The presence of residual glycosylated α-DG in myoblasts is in contrast with that reported in FCMD muscle biopsies (Michele et al., Nature 418(6896): 417-22 (2002)) and similar to a phenomenon of transient reexpression of functional α-DG observed in patients with a mild form of LGMD (Cohn et al., Cell 110(5): 639-48 (2002)), suggesting that fukutin may be differentially expressed at earlier stages of muscle development. However, antibodies to glyco-epitopes of α-DG failed to detect the protein on immunoblot. Consistently, no binding of laminin to α-DG was observed, while ligand-binding activity for neurexin and agrin was considerably diminished and only present in a α-DG fraction of $M_r$ similar to control (FIG. 2b). Following treatment with Ad5-LARGE/eGFP, all transduced cells in control and FCMD cultures expressed glycosylated α-DG (FIG. 2c). Cell viability, proliferation rate, and time and degree of fusion did not vary after transduction with Ad5-LARGE/eGFP. Biochemical changes in α-DG glycosylation were similar to that observed in vivo: core-DG antibodies weakly detected α-DG at higher $M_r$, but failed to recognize heavily glycosylated forms (≧200 kDa) (FIG. 2d). Remarkably, overlay assays demonstrated that LARGE-transfected FCMD myoblasts gained laminin, agrin, and neurexin binding to highly glycosylated α-DG of $M_r$ similar to control (FIG. 2d). Analysis performed at different stages of myoblast differentiation did not reveal significant differences (not shown). Seeing that the retrotransposon insertions in the fukutin gene in FCMD patients leads to marked reduction, but not absence of fukutin (Saito et al., Annals of Neurology 47(6): 756-64 (2000)), we reason that the synthesis of functionally glycosylated α-DG species in FCMD myoblasts by overexpression of LARGE could be either due to enhancement of the residual activity of fukutin or activation of compensatory glycosylation pathways.

To test whether the observed changes were a specific consequence of LARGE overexpression, we treated our cultures with an analogous adenoviral vector expressing eGFP and the full-length human POMGnT1 (Protein O-Mannosyl β-1,2-N-acetylglucosaminyltransferase 1). Although the infection resulted in an over 34-fold increase in POMGnT1 enzyme activity using the substrate Man(α1-)O-benzyl (Zhang et al., Biochem J 361(Pt 1): 153-62 (2002)), we did not observe notable variations in α-DG (FIGS. 2e,f).

Figure 3:
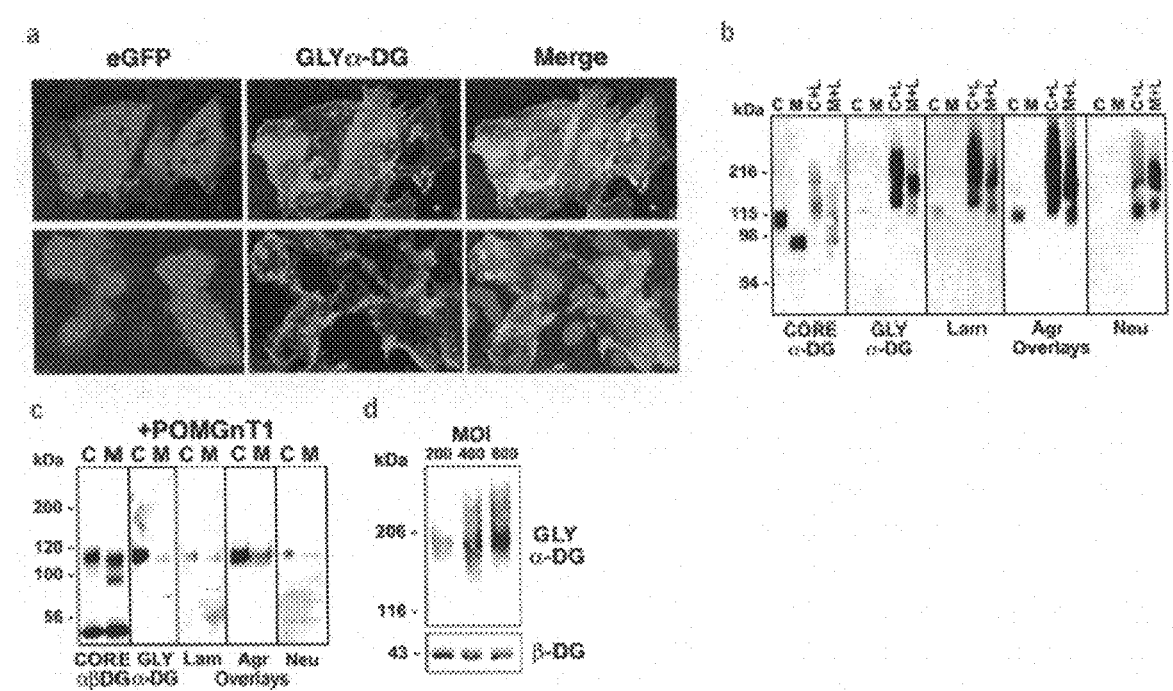
FIG. 3 shows rescue of functional α-DG in MEB fibroblasts. (a) Expression of glycosylated α-DG (GLYα-DG), eGFP, and DAPI nuclear staining in control (C+L) and MEB (M+L) fibroblasts treated with Ad5-LARGE/eGFP. (b) Ligand overlays and immunoblots of WGA-enriched lysates from control and MEB fibroblasts untreated and treated with Ad5-LARGE/eGFP (C, M, and C+L, M+L) using antibodies to α-dystroglycan core protein (COREα-DG) and glycosylated α-DG (GLYα-DG). (c) Ligand overlays and immunoblots of WGA-enriched lysates from control and MEB fibroblasts treated with Ad5-POMGnT1/eGFP. Antibodies to dystroglycan core protein (CORE-αβDG) and glycosylated α-DG (GLYα-DG). Data shown are representative of two patients. (d) Immunoblot analysis of WGA-enriched lysates of control myoblasts infected with Ad5-LARGE/eGFP.

LARGE functionally rescues α-DG in MEB fibroblasts. It has been shown that the rare oligosaccharide NeuAcα2,3 Galβ1,4 GlcNAcβ1,2 Manα-O-Ser/Thr is important in the interaction of α-DG with its ligands (Ervasti and Campbell, J Cell Biol 122(4): 809-23 (1993); Chiba et al., J Biol Chem 272(4): 2156-62 (1997)). POMGnT1 has been proven to be active in this pathway, catalyzing the second step of the synthesis of the tetrasaccharide (Yoshida et al., Developmental Cell 1(5): 717-24 (2001)). To investigate the mechanism of LARGE-dependent glycosylation, we performed LARGE gene transfer in fibroblasts from two siblings affected with MEB. Expression of glycosylated α-DG was detected in control and MEB fibroblasts by immunofluorescence analysis only after treatment with Ad5-LARGE/eGFP (FIG. 3a). Immunoblots with antibodies to DG core peptide detected α-DG species of 115-125 kDa in control and 90 kDa in MEB fibroblasts, while glycosylated α-DG with laminin- and agrin-binding activity was only detected in control cells (FIG. 3b). Treatment with Ad5-LARGE/eGFP generated glycosylated α-DG expression in every transduced control and MEB cell and produced highly glycosylated, functional α-DG (FIG. 3b).

The low but significant levels of POMGnT1 detected in MEB patients are consistent with some proper glycosylation occurring in the presence of mutated POMGnT1 (Michele et al., Nature 418(6896): 417-22 (2002); Zhang et al., Clinical Biochemistry 36(5): 339-344 (2003)). To assess whether LARGE modulates the partially functional enzyme, we evaluated POMGnT1 activity in control and MEB fibroblasts infected with Ad5-LARGE/eGFP or Ad5-eGFP. The 5.9% residual activity of POMGnT1 found in MEB fibroblasts did not vary after LARGE gene transfer. Furthermore, in MEB fibroblasts, POMGnT1 gene transfer resulted in expression of α-DG of $M_r$ comparable to control and restored ligand binding activity (FIG. 3c). However, overexpression of POMGnT1 did not cause changes as dramatic as LARGE. In addition, the relative abundance of LARGE transcript in tissues where α-DG is more heavily glycosylated (Peyrard et al., Proceedings of the National Academy of Sciences of the United States of America 96(2): 598-603 (1999)), and the finding that high levels of LARGE generate heavily glycosylated α-DG species, suggest that levels of LARGE may be a limiting factor in α-DG glycosylation. Indeed, treatment of human control cells with Ad5-LARGE/eGFP at increasing MOI corresponded to synthesis of α-DG of increasing $M_r$ (FIG. 3d). These results demonstrate that induction of LARGE can activate compensatory glycosylation mechanisms of α-DG in a dose-dependent fashion.

Figure 4:
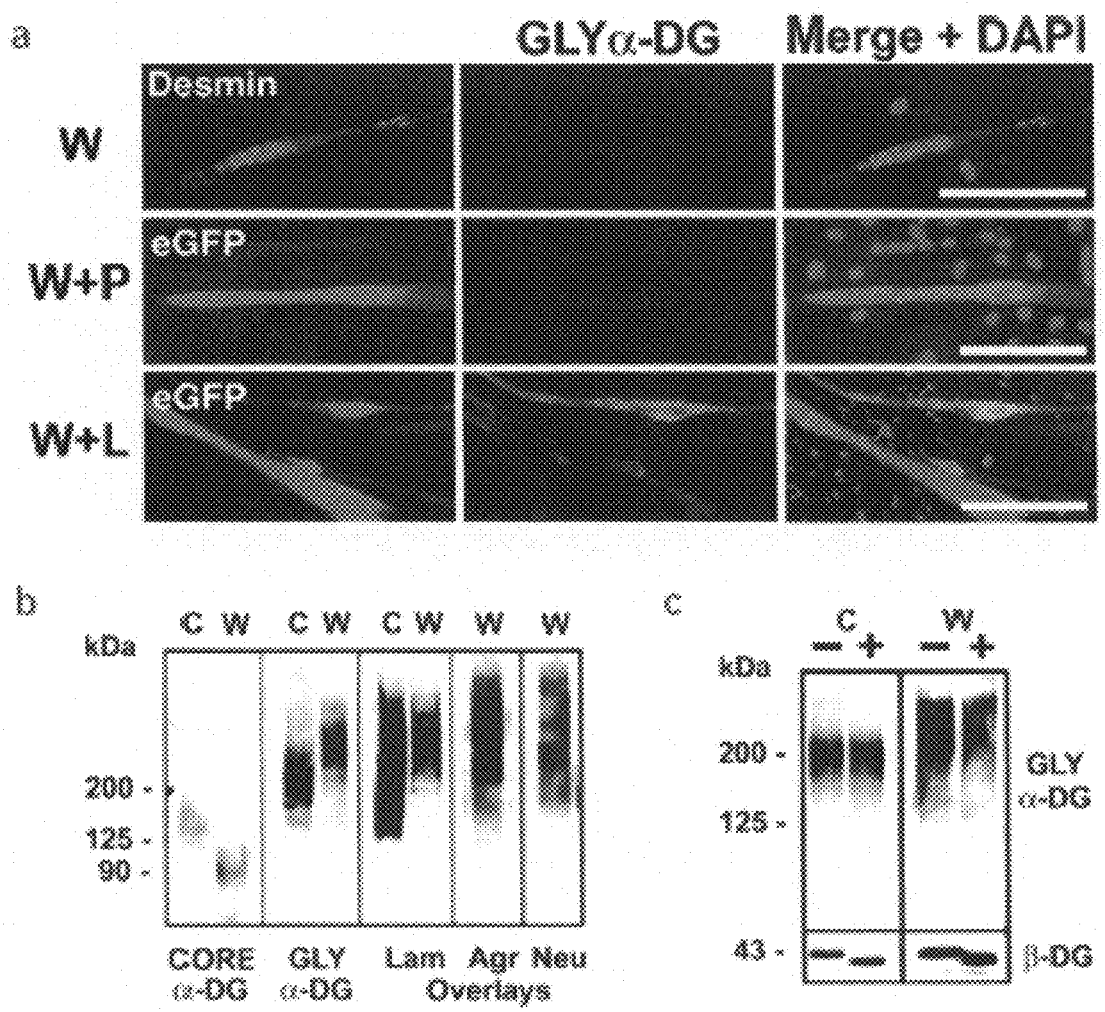
FIG. 4 illustrates that LARGE induces the synthesis of functional α-DG in WWS cells. (a) Expression of eGFP, desmin, glycosylated α-DG (GLYα-DG), and nuclear labelling (DAPI) in WWS myoblasts untreated (W) and treated with Ad5-LARGE/eGFP (W+L) or Ad5-POMGnT1/eGFP (W+P). Scale bar 20 µm. (b) Biochemical analysis of WGA-enriched fractions from control (C) and WWS myoblasts (W) treated with Ad5-LARGE/eGFP. Immunoblots performed with antibodies to glycosylated α-DG (GLYα-DG) and α-DG core protein (COREα-DG). Laminin (Lam), agrin (Agr), and neurexin (Neu) ligand overlay assays. (c) N-Glycanase deglycosylation of WGA-enriched fractions from control (C) and WWS myoblasts (W) treated with Ad5-LARGE/eGFP. Immunoblot with antibodies to β-DG and glycosylated α-DG (GLYα-DG). Untreated samples (−) are shown. Data shown are representative of four patients.

LARGE generates functional α-DG in WWS cells. To further investigate whether the extensive glycosylation of α-DG following LARGE gene transfer is due to the synthesis of novel glycan chains that are normally absent or less represented in skeletal muscle, we performed LARGE gene transfer on myoblast and fibroblast cell lines from four WWS patients. Myoblasts of one of the patients were mutated in the gene encoding for Protein O-Mannosyltransferase 1 (POMT1), which catalyzes the first step of the O-mannose linked glycan motif of α-DG (Jurado et al., Genomics 58(2): 171-80 (1999)). As also described for WWS skeletal muscle (Jimenez-Mallebrera et al., Eur J Paediatr Neurol 7(3): 129-37 (2003)), glycosylated α-DG was not seen at any stage in WWS cell cultures, and immunoblot analysis revealed the presence of hypoglycosylated α-DG (FIG. 4a and not shown). Following treatment with Ad5-LARGE/eGFP, but not Ad5-POMGnT1/eGFP, staining for glycosylated α-DG was observed in transduced cells (FIG. 4a). In all the WWS cell lines examined, treatment with Ad5-LARGE/eGFP led to the synthesis of α-DG species in the higher range of $M_r$ compared to control, while residual hypoglycosylated α-DG was still found (FIG. 4b). Importantly, hyperglycosylation correlated with rescue of function of α-DG as a receptor for its extracellular ligands (FIG. 4b). These results indicate that induction of LARGE leads to functional glycosylation of α-DG on alternative O-linked residues.

Figure 5:
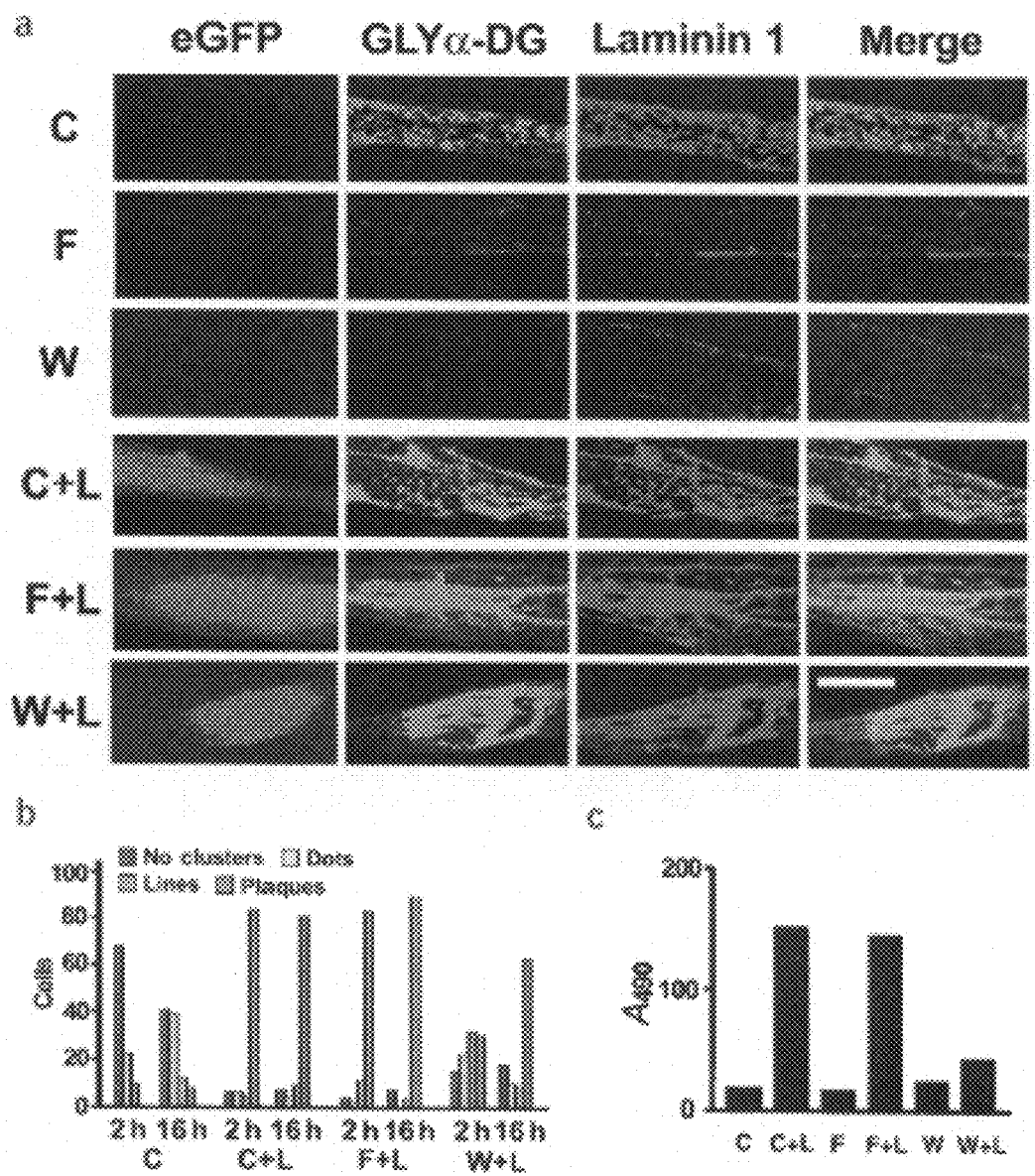
FIG. 5 shows laminin clustering correlates with high α-DG-laminin affinity. (a) Immunofluorescence localization of glycosylated α-DG (GLYα-DG), laminin-1, and eGFP after 16 hours incubation with laminin-1. Scale bar is 20 µm. Not infected (C, F, W) and Ad5-LARGE/eGFP-treated (C+L, F+L, W+L) control, FCMD and WWS myoblasts. (b) Kinetic analysis of laminin-1 cluster formation after 2 and 16 hours incubation with laminin-1. Approximately 100 cells evaluated for each group. (c) Solid-phase assay of α-DG-laminin maximum binding at 0.6 nM of laminin-1 in control, FCMD, and WWS WGA-enriched glycoproteins from not infected (C, F, W) and Ad5-LARGE/eGFP-treated (C+L, F+L, W+L) myoblasts.
Figure 6:
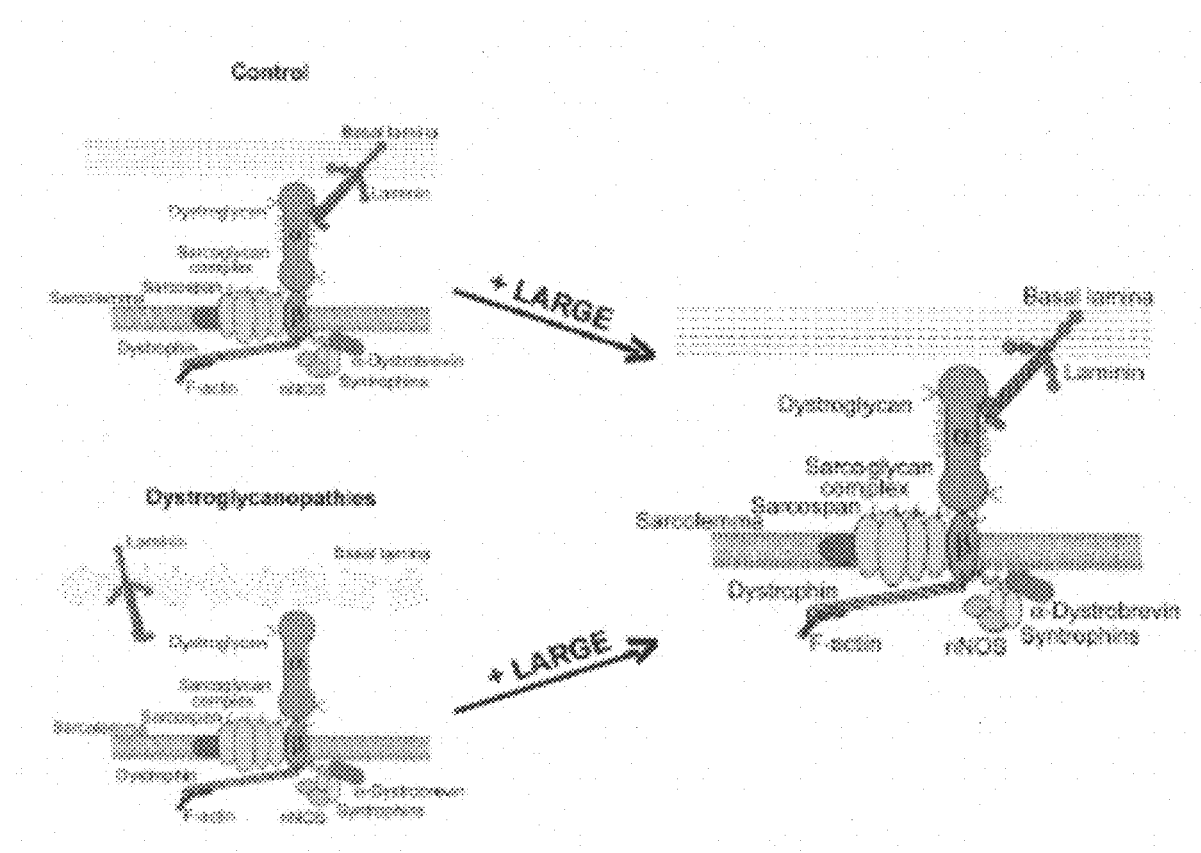
FIG. 6 shows the effect of LARGE on α-DG glycosylation. Schematic representation of the effect of overexpression of LARGE in control and patients' skeletal muscle. See text for details.

Since the sialyl N-acetyllactosamine moiety involved in the interaction of α-DG with its ligands is also a common constituent of many N-glycans, WGA-enriched fractions of treated control and WWS cells were subjected to enzymatic deglycosylation using N-Glycanase. Enzyme activity was verified by complete N-deglycosylation of β-DG. $M_r$ of α-DG did not change after enzymatic treatment, confirming the predominance of O-linked oligosaccharides (FIG. 4c). In addition, reactivity for glycosylated α-DG disappeared after alkaline O-deglycosylation (not shown). Furthermore, our attempts at enzymatic deglycosylation with exoglycosidases for sugars putatively added by LARGE have failed to release any sugars. These data suggest either that LARGE modulates the activities of other as yet undetermined enzymes thereby affecting an alternative glycosylation pathway of α-DG, or LARGE activity may be different from that predicted by homology of its catalytic domains.

α-DG-laminin affinity facilitates laminin clustering. The perturbation of the basement membrane described in FCMD and WWS muscle is an important pathogenetic event in many congenital muscular dystrophies (Ishii et al., Neuromuscul Disord 7(3): 191-7 (1997); Sabatelli et al., Biochim Biophys Acta 1638(1): 57-62 (2003)). We examined the ability of glycan-enriched α-DG to coordinate the assembly of extracellular matrix proteins by analyzing the formation of exogenous laminin-1 clusters on differentiating myoblasts. DG-mediated laminin clustering is a dynamic process in which small dot-shaped clusters merge into complex structures (Cohen et al., J Cell Biol 136(5): 1047-1058 (1997); Henry and Campbell, Cell 95(6): 859-70 (1998)). Very little endogenous laminin-1 was on the surface of control cells before treatment (not shown). Within 2 hours of incubation with laminin-1, only a small number of cells displayed dot-like clusters. By 16 hours, a larger number of cells were found positive for laminin clusters and a small percentage of myoblasts bearing linear and small plaque-like clusters was observed (FIGS. 5a, b). In FCMD and WWS cultures, a small amount of exogenous laminin bound to the cell surface but failed to organize into complex structures (FIG. 5a). A dramatic change in clustering was observed after LARGE viral treatment: complex plaques formed within 2 hours in all cultures. In control and FCMD, plaques were the predominant cluster type, and the distribution of cells with dot, linear, and plaque-like clusters remained stable over 16 hours. In WWS myoblasts, the punctate pattern of laminin progressed into organized arrays more slowly (FIG. 5b). Importantly, laminin always colocalized with glycosylated α-DG. Similar results were obtained in Large$^{myd}$ myoblasts after LARGE gene transfer (not shown). In addition, the laminin binding activity in control myoblast cultures was very low, and we were not able to measure significant differences among control, FCMD, and WWS samples by quantitative solid-phase assays. Forced expression of LARGE strikingly increased maximum laminin binding and affinity in control and FCMD and to a lesser degree in WWS cells (FIG. 5c). We conclude that very low binding activity is adequate for α-DG to perform as a receptor for extracellular matrix proteins, however the efficiency in assembling and remodeling the extracellular matrix increases with higher affinity of α-DG for its ligands. As the receptor activity of α-DG is restored by induction of LARGE, it is likely the mechanical properties of diseased muscle fibers would be improved.

Methods

Antibodies. VIA4-1 and IIH6 are monoclonal antibodies to fully glycosylated species of α-DG (Ervasti and Campbell, Cell 66(6): 1121-31 (1991)). The antibodies were used interchangeably, and are referred as GLYα-DG in the text, however most of the data shown represent staining obtained with IIH6. GT20ADG (COREα-DG) is from goat antiserum raised against the entire DGC and purified against a hypoglycosylated full-length α-DG-human IgGFc fusion protein (Kunz et al., J Cell Biol 155(2): 301-10 (2001); Michele et al., Nature 418(6896): 417-22 (2002)). CORE-αβDG is from sheep polyclonal antiserum to the entire DGC and recognizes both α- and β-DG (Ibraghimov-Beskrovnaya et al., Nature 355(6362): 696-702 (1992)). Polyclonal antibodies to DGC components were used as described previously (Duclos et al., J Cell Biol 142(6): 1461-71 (1998)). Rabbit polyclonal anti-laminin 1 and mouse monoclonal anti-desmin were from Sigma; mouse monoclonals anti-agrin and anti-caveolin-3 were from Chemicon and Transduction Laboratories, respectively.

Mice. Myodystrophy mice (Large$^{myd}$) and control littermate mice (Large$^{+/+}$ or Large$^{myd/+}$) were obtained by mating heterozygous pairs provided by Jackson Laboratories. All animals were maintained at the University of Iowa Animal Care Unit in accordance with animal usage guidelines.

Adenovirus generation and infection. E1-deficient recombinant adenovirus Ad5-LARGE/eGFP and Ad5-POMGnT1/eGFP that carry the enhanced green fluorescent protein (eGFP) and the entire ORF of the human LARGE or the human POMGnT1 in trans, respectively, were generated by the University of Iowa Gene Transfer Vector Core. Transcription of LARGE or POMGnT1 was initiated by the cytomegalovirus promoter (CMV); transcription of eGFP was initiated by the Rous sarcoma virus promoter (RSV). Translation of the transcripts yielded LARGE or POMGnT1 and eGFP as separate proteins. In vivo gene transfer was performed on two- to four-days old Large$^{myd}$ and littermate pups as described (Durbeej et al., Proc Natl Acad Sci USA 100(15): 8910-5 (2003)). Injected and non-injected contralateral leg muscles were examined four weeks later. Cell cultures were infected with viral vector for 12 h with multiplicity of infection (MOI) between 200 and 800. At this concentration, cytotoxicity was <15% of the cells. Cultures were examined 3-10 days post-treatment.

Immunohistochemical analysis. Cryosections (7 μm) were processed for immunofluorescence as described (Duclos et al., J Cell Biol 142(6): 1461-71 (1998)). Cultured cells were fixed in 4% paraformaldehyde before incubation with primary antibodies. Slides were observed with a Bio-Rad MRC-600 laser scanning confocal microscope. Digitised images were captured under identical conditions.

Glycoprotein enrichment and biochemical analysis. Frozen samples and cultured cells were processed as described (Michele et al., Nature 418(6896): 417-22 (2002)). Immunoblots and ligand overlay assays were performed on PVDF membranes as described (Michele et al., Nature 418(6896): 417-22 (2002)). Blots were developed by HRP-enhanced chemiluminescence (Pierce). N-deglycosylation was performed using N-Glycanase (ProZyme) according to the manufacturer's instructions. Solid-phase binding assay was performed as described (Michele et al., Nature 418(6896): 417-22 (2002)).

Treadmill Exercise. Animals were exercised using the Omnipacer™ treadmill (Accuscan Instruments). Model LC4/M-MGA/AT (Accuscan Instruments, Inc., Columbus, Ohio) at a 15° downward angle during increasing speed up to 19 m/min for 30 min. 5-7-weeks old Large$^{myd}$ and littermate mice injected with LARGE adenovirus in the right hamstrings were utilized (n=4). All mice were injected with Evans blue dye (EBD) intraperitoneally 5 hours prior to exercise. Mice were euthanized 24 hours following exercise and sections of right and left hamstrings were compared for EBD uptake and glycosylated α-DG expression. Quantification of EBD positive stained areas in sections of skeletal muscle was done using the ImageJ software (NIH). The percentage of positive stained areas was calculated by dividing the area of staining by the total area of the analyzed skeletal muscle section.

Patients' cells. MEB fibroblasts were from two compound heterozygote siblings with a G1908A transversion in exon 21 (Arg605His) in one allele and a single base pair insertion in exon 11 in the other allele (1106insT causing a frameshift and premature termination at codon 338) in the POMGnT1 gene (Zhang et al., Clinical Biochemistry 36(5): 339-344 (2003)). FCMD myoblasts were from three Japanese patients. One of the patients was homozygous for the retrotransposon insertion in the fukutin gene (Kobayashi et al., Nature 394(6691): 388-92 (1998)). The other two patients were heterozygous for the insertion and either Cys250Gly or Leu353Stop (+polymorphism Arg203Glu). WWS myoblasts were from a Japanese boy homozygous for Leu421deI in POMT1, and a 6 month-old Hispanic male (Kanoff et al., Pediatr Neurol 18(1): 76-80 (1998)). WWS fibroblasts were from a 3 year-old female and a 4 year-old male with clinical diagnosis of WWS. In these patients the analysis of the full-length POMT1 and POMGnT1 cDNA did not detect mutations. Dystroglycan cDNA regions corresponding to laminin-binding domains and glycosylated domains were normal. All tissues were obtained and tested in agreement with the Human Subjects Institutional Review Board of the University of Iowa.

Cell cultures. Cells were maintained at 37° C., 5% $CO_2$ in DMEM+20% fetal bovine serum, 0.18 μg/ml insulin, 0.5% penicillin/streptomycin (Gibco). The ratio myoblasts to fibroblast estimated by desmin staining was 1:7 in control and FCMD, and 1:5 in WWS cultures. Myoblast fusion was obtained by decreasing the serum concentration to 2% (differentiation medium). For the laminin clustering assay, myoblasts were switched to fresh differentiation medium containing 7.5 nM mouse EHS laminin-1 and incubated for 2, 5, and 16 hours. Confocal immunofluorescence images were compiled from a 5 μm z-series extending from the dorsal surface of the cells in 0.5 μm steps. Morphological evaluation of clusters was performed as described (Henry et al., J Cell Sci 114(Pt 6): 1137-44 (2001)).

Example 2

Figure 7:
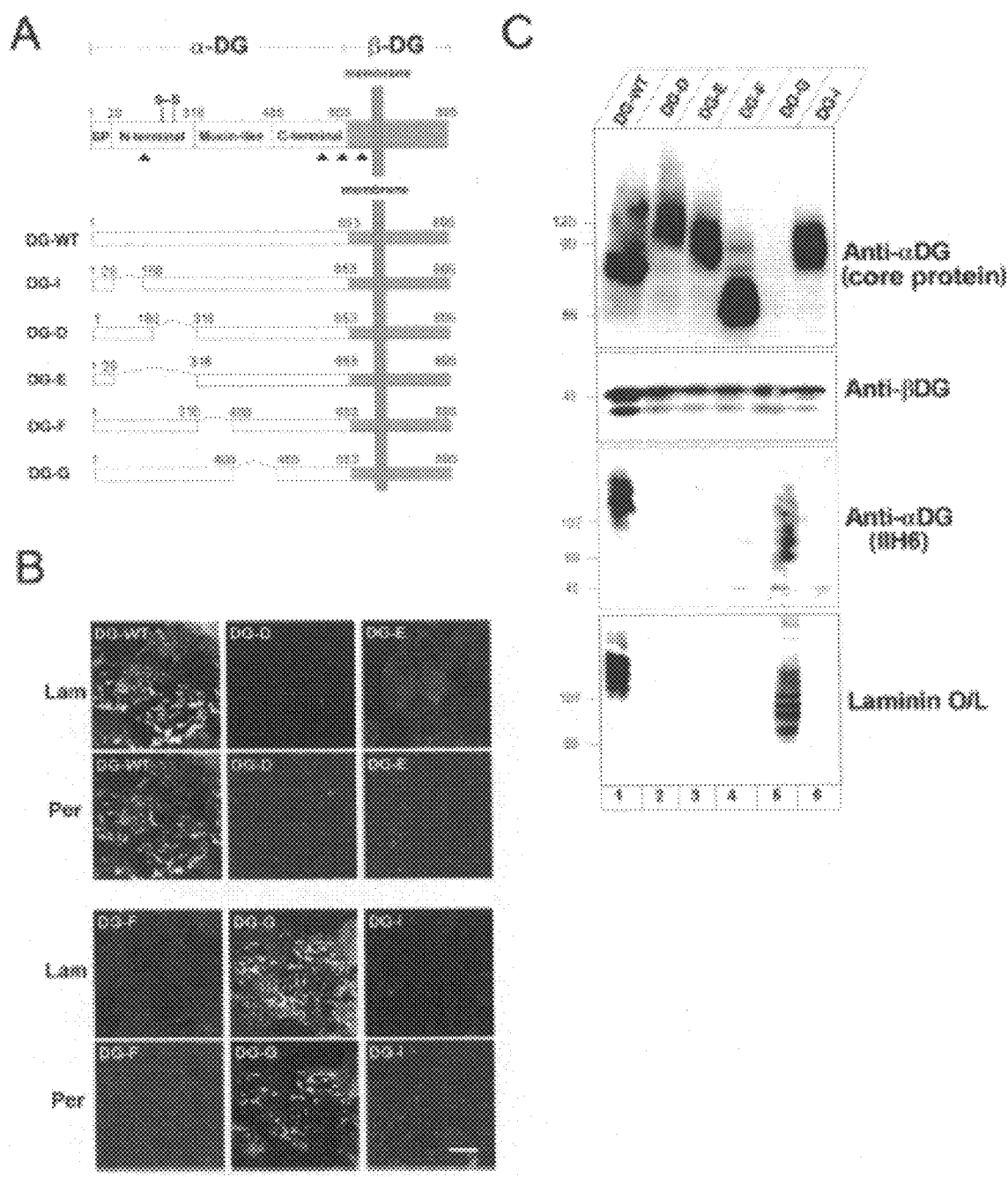
FIG. 7 shows an analysis of α-DG functional domains. Schematic representation of DG deletion mutant proteins. α-DG is composed of a signal peptide (SP, amino acids 1-29), an N-terminal domain (amino acids 30-316), a mucin-like domain (amino acids 317-485) and a C-terminal domain (amino acids 486-653). The disulfide bond is shown by S-S and potential N-glycosylation sites are indicated by arrowheads. The hatched box represents β-DG. B) The N-terminal domain of α-DG is necessary for cell surface laminin and perlecan organization. Laminin-1 (Lam) and perlecan (Per) form clusters of plaque-like morphology on the surface of cells expressing DG-WT and DG-G. Bar, 10 µm. C) Both the N-terminal domain and the first-half of the mucin-like domain (amino acids 30-408) of α-DG are necessary for laminin binding. Western blotting and laminin overlay (O/L) assays show that laminin-1 binds to DG-WT and DG-G.

Molecular Recognition by LARGE is Essential for Expression of Functional Dystroglycan Results
Post-Translational Modification Regulates Laminin-Receptor Function of DG To examine the nature of the α-DG-laminin interactions, we generated a set of adenovirus (AdV)-constructs with deletions in the N-terminal and/or the mucin-like domain of α-DG (FIG. 7A). These deletion constructs, when expressed in embryonic stem (ES) cells, can properly target α- and β-DG proteins to the cell surface membrane (Kunz et al., 2001). First, we performed a laminin-1 and perlecan clustering assay on DG-null ($DG^{-/-}$) ES cells after infection with each AdV-construct to define the DG domains necessary for DG-mediated basement membrane assembly. Laminin-1 and perlecan formed clusters, which consolidated into plaque-like morphologies, on the surface of ES cells expressing DG-WT or DG-G. No clusters were observed on the cells expressing DG-I, DG-D, DG-E or DG-F (FIG. 7B). Next, the laminin-binding domain was characterized by blot overlay assay. Because antibodies against α-DG do not recognize all of the deletion mutants, the protein amount was adjusted by immunoreactivity against β-DG (FIG. 7C). Laminin-1 bound to DG-WT and DG-G (FIG. 7C). The monoclonal antibody IIH6, whose epitope is sensitive to the glycosylation status of α-DG (Ervasti and Campbell, 1993), also detected only DG-WT and DG-G. Unexpectedly, the results demonstrated that in addition to the N-terminal half of the mucin-like domain, the whole N-terminal domain of α-DG is necessary for laminin- and IIH6-binding as well as laminin-1 and perlecan organization on the cell surface.

Figure 8:
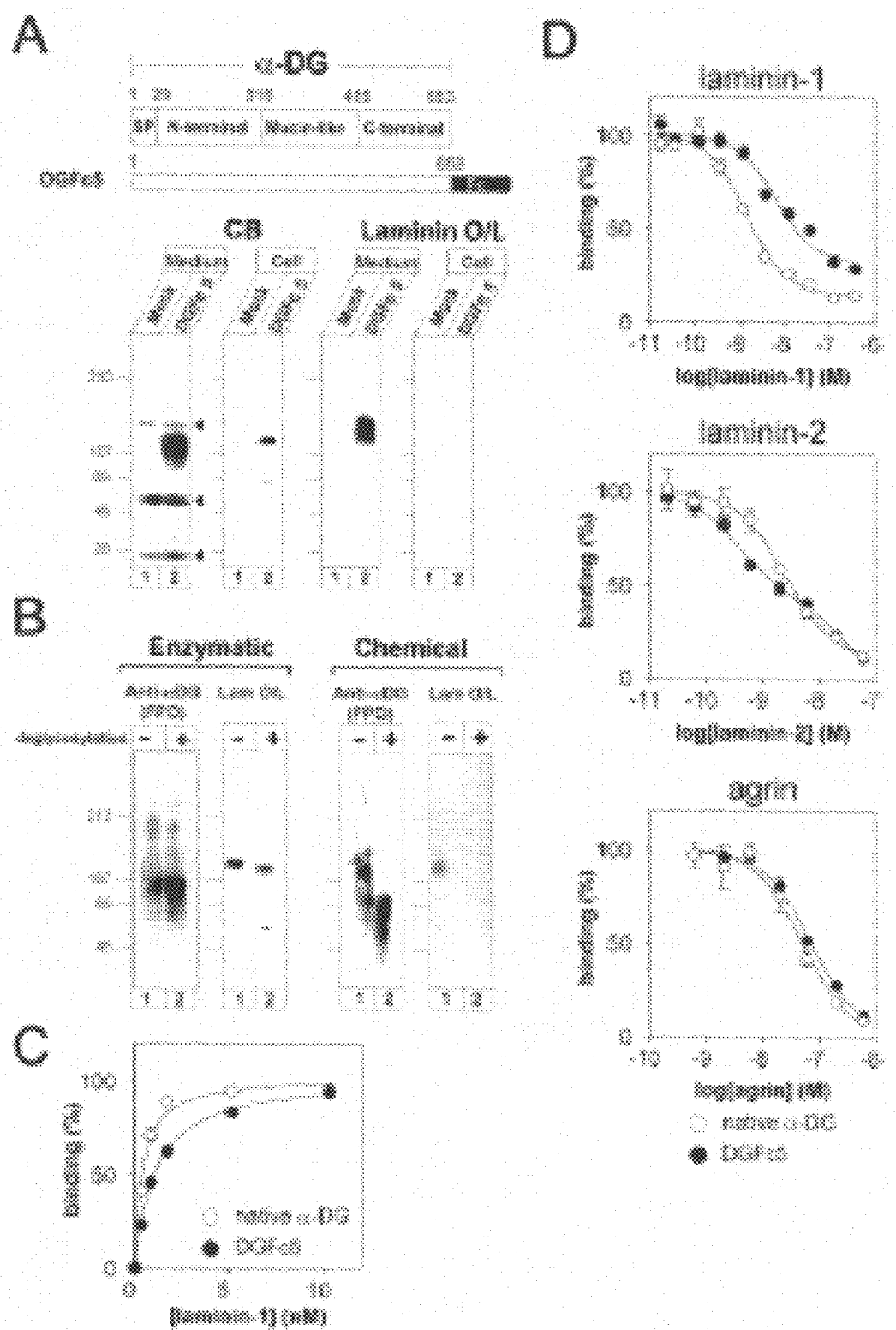
FIG. 8 shows expression of full-length α-DG-IgG Fc fusion protein (DGFc5) and its interaction with laminin. DGFc5 was purified from the conditioned medium or cell lysate. Arrowheads indicate contaminated immunoglobulin light chain, heavy chain and heavy chain dimer. O/L, overlay. A) Laminin-1 binds to DGFc5 in conditioned medium but does not bind that in cell lysate. A population of DGFc5 to which laminin-1 binds migrates slower than that stained by CB. Lane 1, mock transfection; Lane 2, transfection with DGFc5. Schematic representation of DGFc5 is shown at the top of panel A. Black boxes indicate the Fc portion. B) Glycosylation is essential for laminin-binding activity of DGFc5. DGFc5 was deglycosylated either enzymatically or chemically. By chemical deglycosylation, the molecular mass of DGFc5 is greatly reduced and laminin-binding is abolished. Lane 1, untreated sample; Lane 2, treated sample for deglycosylation. C) Binding of laminin-1 to DGFc5 (closed circle) and native α-DG (open circle). By nonlinear regression analysis, the dissociation constants of DGFc5 and native α-DG are estimated to be 1.1±0.1 and 0.4±0.1 nM, respectively. D) DGFc5 represents similar ligand selectivity to native α-DG. Competitive binding of biotinylated laminin-1 to native α-DG (open circle) or DGFc5 (closed circle) was measured in the presence of non-labeled laminin-1, laminin-2 and agrin. All non-labeled ligands compete the binding of biotinylated laminin-1 to both native α-DG and DGFc5.

To further investigate the interaction between α-DG and laminin, we generated full-length and truncated α-DG molecules as IgG Fc fusion proteins (DGFc) by transfecting TSA201 cells. The majority of the expressed full-length fusion protein (DGFc5) was secreted as a 100-120 kDa protein into the culture media although some was detected in the cell lysate. We observed, by blot-overlay assay, that laminin-1 bound to the secreted DGFc5, but not to DGFc5 in the cell lysate (FIG. 8A). Interestingly, the species of DGFc5 that binds to laminin migrates slower than that stained by Coomassie blue (CB). Antibody FPD, against the core protein of α-DG, identified broader bands than those stained by CB (FIG. 8B). Laminin and IIH6 reacted to the slow migrating species of the FPD-reactive bands (data not shown). This broad appearance of the fusion protein suggests extensive post-translational modification, as is the case with native α-DG in skeletal muscle (Ervasti and Campbell, 1991). Enzymatic deglycosylation slightly decreased the molecular mass of DGFc5 and did not affect laminin-binding activity (FIG. 8B). However, chemical deglycosylation greatly reduced the molecular mass and abolished laminin-binding activity. These results are consistent with previous observations that the sugar chain structure of α-DG is necessary for the interaction with laminin (Ervasti and Campbell, 1993). It is evident that only a small population in the DGFc5 preparations possess the specific carbohydrate modification required for ligand-binding activity. Taken together, these data indicate that strict post-translational glycosylation is necessary for the interaction between α-DG and laminin.

To confirm that DGFc5 conserves the ligand-binding properties of native α-DG, we demonstrated that DGFc5, when compared to native α-DG, has similar laminin-binding affinity (FIG. 8C), can quantitatively compete laminin-binding to native α-DG (data not shown), and shows similar ligand selectivity by non-labeled ligand competition assays (FIG. 8D).

LARGE-Dependent Functional Modification of α-DG

Figure 9:
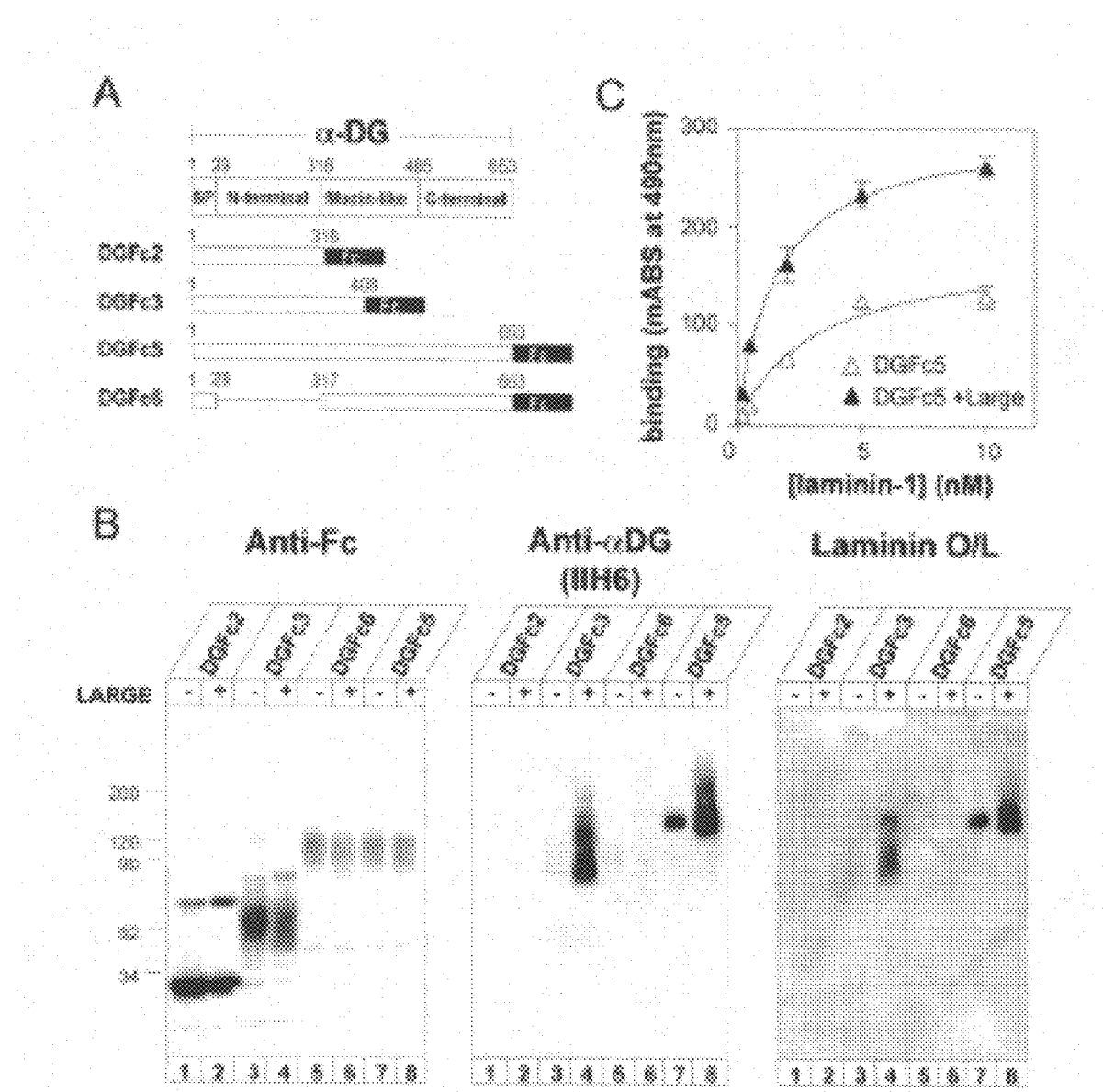
FIG. 9 shows that LARGE-dependent glycosylation requires the N-terminal half of α-DG. A) Schematic representation of deletion mutants of DGFc proteins. B) The N-terminal domain and the first-half of the mucin-like domain of α-DG is necessary for LARGE-dependent glycosylation. Western blotting and laminin overlay (O/L) assay shows that DGFc3 and DGFc5 are functionally glycosylated by LARGE. Neither the N-terminal nor the mucin-like domain itself are sufficient for the functional glycosylation by LARGE and/or intrinsic glycosyltransferases. C) LARGE-dependent glycosylation of DGFc5 increases laminin-binding activity. By nonlinear regression analysis, the dissociation constants of DGFc5 (open triangles) and LARGE-modified DGFc5 (closed triangles) to laminin-1 are estimated to be 3.1±1.1 and 1.6±0.1 nM, respectively.

We recently demonstrated that forced expression of LARGE produced glycan-rich α-DG species and restored its function as a laminin-receptor in FCMD, MEB, and WWS patients' cells (Barresi, et al., 2004). We investigated the molecular mechanism for LARGE-dependent functional modification of DG using DGFc fusion proteins. Several deletion constructs of DGFc proteins were generated and expressed in TSA201 cells (FIG. 9A). Ligand overlay assays on these fusion proteins further confirmed our previous results in ES cells: both the N-terminal domain and the first half of the mucin-like domain are essential for DG function as an ECM-receptor. Furthermore, adenoviral expression of LARGE with each DGFc fusion protein increased reactivity to 11H6 and laminin-1-binding in the secreted form DGFc3 and DGFc5, but not in DGFc2 and DGFc6 (FIG. 9B). However, in cell lysates, regardless of LARGE overexpression, we did not observe significant reactivity of any DGFc proteins to laminin-1 or 11H6 even when detection sensitivity was increased and/or the fusion protein was loaded in equal amounts compared to the secreted DGFc protein experiments. A solid-phase laminin-1 binding assay on secreted DGFc5 demonstrated that LARGE-modification quantitatively increased the laminin-1-binding activity (FIG. 9C). Although DGFc6 contains the entire mucin-like domain, we did not see any functional modification of DGFc6 even after the LARGE overexpression, suggesting that the N-terminal domain is required for the functional modification by either LARGE or other intrinsic glycosyltransferases. Notably, the secreted form of DGFc5 and DGFc6 migrated with similar molecular weight on SDS-PAGE, and the majority of DGFc2 prepared from conditioned medium seemed to be degraded. These findings led us to hypothesize that the N-terminal domain was proteolytically processed. We found that culturing TSA201 cells expressing DGFc2 in the presence of decanoyl-Arg-Val-Lys-Arg-CMK (CMK) (SEQ ID NO: 15), an inhibitor for proprotein convertases (endoprotease family), prevented degradation of DGFc2. Accordingly, the secreted DGFc2 migrated at the same molecular size (~65 kDa) as DGFc2 prepared from cell lysate. Neither preparation showed any detectable laminin-binding activity, with or without LARGE coexpression (data not shown). These data also support previous findings that essential glycosylation indeed occurs in the mucin-like domain.

Figure 10:
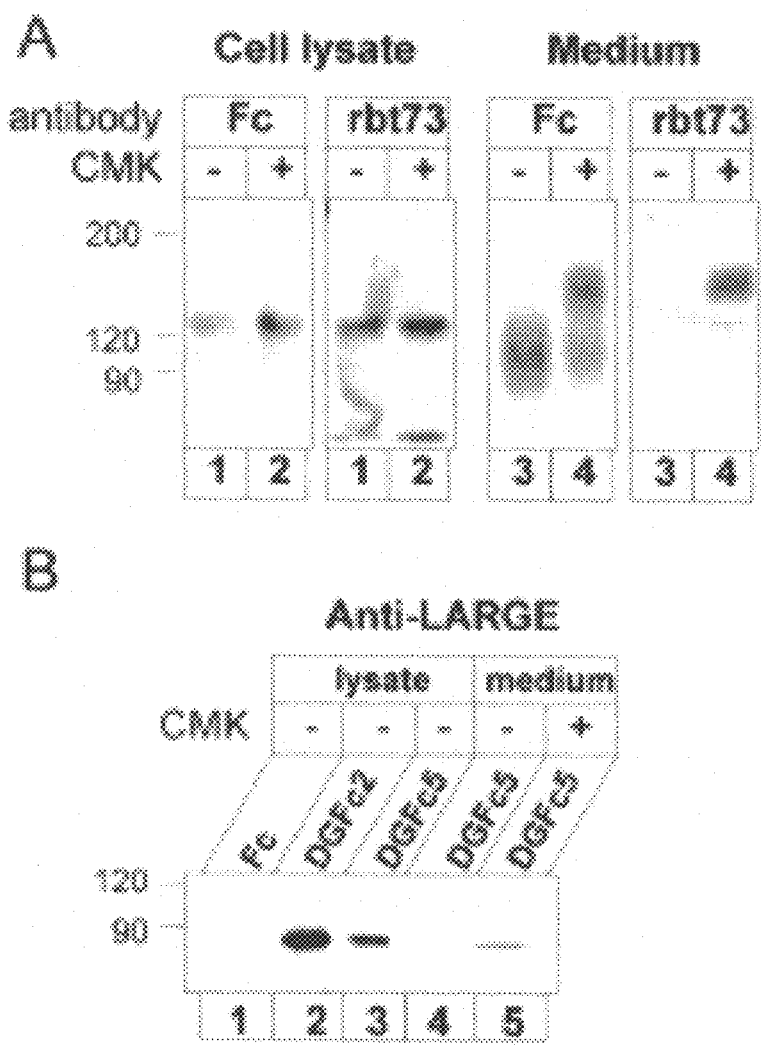
FIG. 10 illustrates a mechanism for glycosylation of α-DG by LARGE. A) Proteolytical processing of the N-terminal domain of α-DG. Western blotting analysis with antibodies to the Fc or the N-terminal sequence of α-DG (rbt73) reveal that the secreted form of DGFc5 lacks its N-terminal domain. DGFc5 in cell lysates contains its N-terminal domain. Treatment with a convertase inhibitor, CMK, prevents proteolytic processing of the N-terminal domain of the secreted form of DGFc5. B) Molecular interaction between α-DG and LARGE. The following DGFc-protein A-beads were prepared and then incubated with LARGE-expressing TSA201 cell lysate. Fc (cell lysate), DGFc2 (cell lysate), DGFc5 (cell lysate), DGFc5 (medium), and DGFc5 (CMK-treated, medium). Western blotting with anti-LARGE antibody demonstrates that LARGE recognizes the N-terminal domain of α-DG to form an enzyme-substrate intermediate complex.

A molecular weight shift following protease inhibition was also found in secreted DGFc3 and DGFc5, but not in DGFc6 (data not shown). CMK-treatment caused secreted DGFc5 to migrate around 150 kDa and become reactive to an antibody to an N-terminal peptide of α-DG (rabbit 73) (FIG. 10A). Without the CMK-treatment, no significant reactivity to rabbit 73 was obtained with DGFc5 prepared from cell culture media. On the other hand, the DGFc5 preparations from cell lysate showed reactivity against rabbit 73 regardless of CMK-treatment (FIG. 10A). These data suggest that a convertase-like activity processes the N-terminal domain of α-DG as it is secreted from cells or in the extracellular environment. N-terminal amino acid sequence analyses of DGFc5 from CMK-treated cells and full length DGFc5 cleaved by furin in vitro revealed that a convertase-like activity cleaves α-DG between $Arg^{312}$ and $Gln^{313}$.

Our evidence of proteolytic processing of the N-terminal domain of secreted DG excluded the possibility that the ternary structure of the N-terminal domain is directly required for laminin binding to the mucin-like domain. Since DGFc5 isolated from cells contains the N-terminal domain, we hypothesized that the N-terminal domain may be required intracellularly for transient recognition by glycosyltransferases to form the enzyme-substrate intermediate. To test this hypothesis, we examined molecular interactions between LARGE and DGFc proteins. Protein-A affinity beads coupled to DGFc proteins were incubated with LARGE-overexpressed TSA201 cell lysates. Bound materials were eluted with Laemmli sample buffer (LSB) and analyzed by Western blotting using an anti-LARGE antibody (FIG. 10B). We found that LARGE interacted with DGFc2 (lane 2), and DGFc5 prepared from cell lysate (lane 3). Importantly, although the secreted form of DGFc5 did not bind LARGE (lane 4), inhibition of proteolytic cleavage with CMK successfully reconstituted the DGFc5-LARGE complex (lane 5). Mature glycosylation does not seem to affect the interaction between α-DG and LARGE. Together, these data suggest that the N-terminal domain of α-DG is recognized by LARGE to form the enzyme-substrate intermediate, which is necessary for the subsequent glycosylation on the first-half of the mucin-like domain. The N-terminal domain is then proteolytically cleaved after the glycosylation occurs.

In Vivo Evidence for Significance of DG-LARGE Interaction

Figure 11:
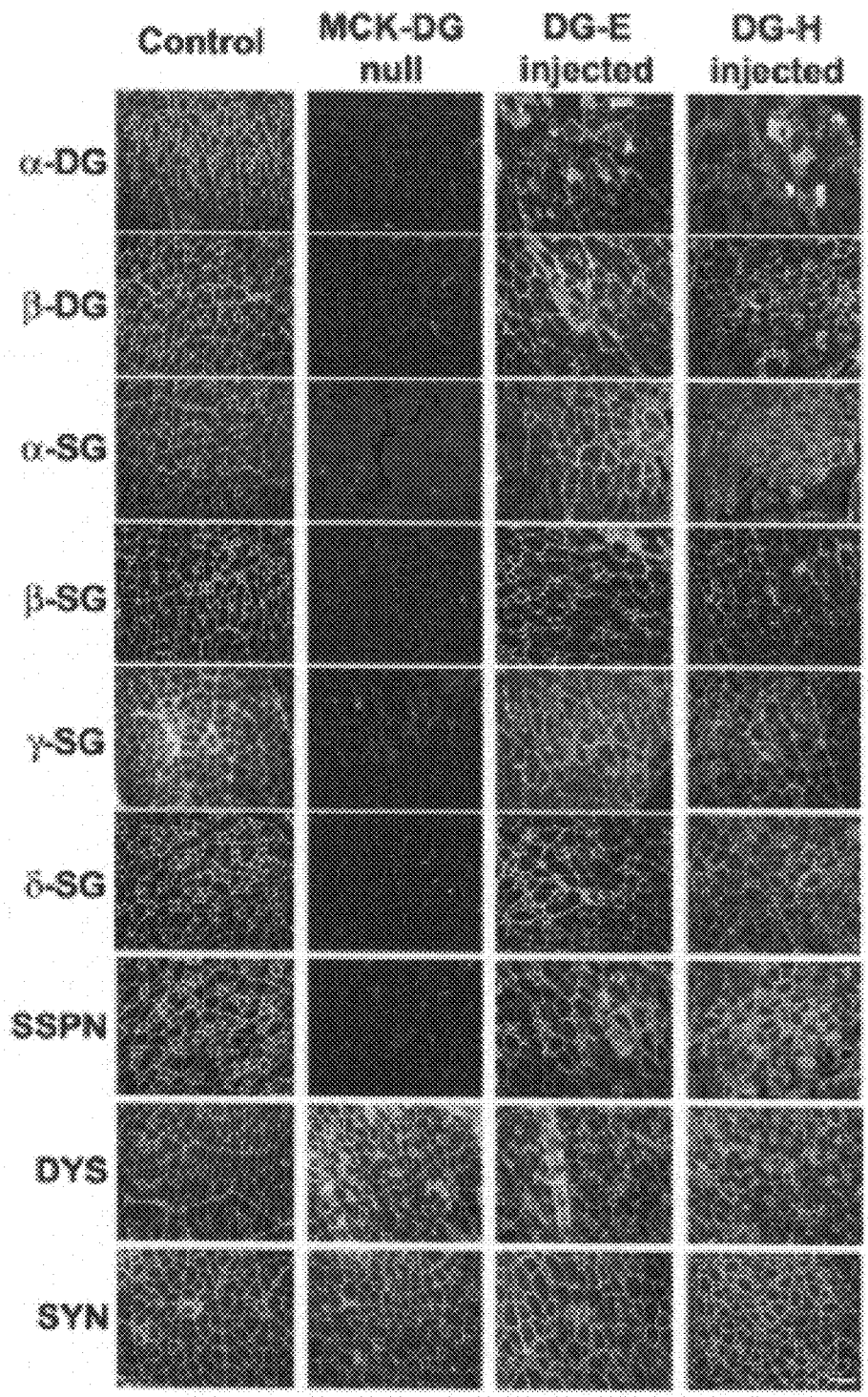
FIG. 11 shows restoration of the DGC in skeletal muscle of MCK-DG null mice expressing DG deletion mutant proteins. The C-terminal domain of α-DG and/or β-DG are responsible for the DGC assembly. The DGC assembly was examined by immunofluorescence analysis after expression of deletion mutants of DG in vivo. The figure shows DG-E- and DG-H-injected skeletal muscle, which represent all constructs tested. All the DGC components are restored at the sarcolemma after gene transfer. The equivalent results were obtained by expressing DG-WT, DG-I, DG-D, DG-F, or DG-G. SG, sarcoglycan; SSPN, sarcospan; DYS, dystrophin; SYN, syntrophin.

In order to determine the significance of the molecular recognition of the N-terminal domain by LARGE, and the functional glycosylation of α-DG in vivo, we expressed deletion mutants of DG in skeletal muscle of MCK-DG null mice in which the endogenous DG gene is selectively ablated in striated muscle. MCK-DG null mice show concomitant loss of sarcoglycans and sarcospan, and develop muscular dystrophy at 4-5 weeks of age (Cohn et al., 2002). Five weeks after viral gene transfer, more than 80% of the muscle fibers were transduced and converted to DG positive in each of the injected mice (FIG. 11). Interestingly, each of the expressed DG proteins (DG-WT, DG-I, DG-D, DG-E, DG-F, DG-G) restored the DGC assembly at the sarcolemma including sarcoglycans and sarcospan. The expression of a shorter DG-H protein lacking the entire N-terminal and mucin-like domains of α-DG also restored the DGC assembly. In FIG. 11, the expression profile is represented by DG-E and DG-H. Dystrophin and α1-syntrophin, which are preserved in MCK-DG null mice, were also normally expressed in these muscles. These results provide novel evidence that the C-terminal domain of α-DG and/or β-DG mediate the stable assembly of the DGC at the sarcolemma.

Figure 12:
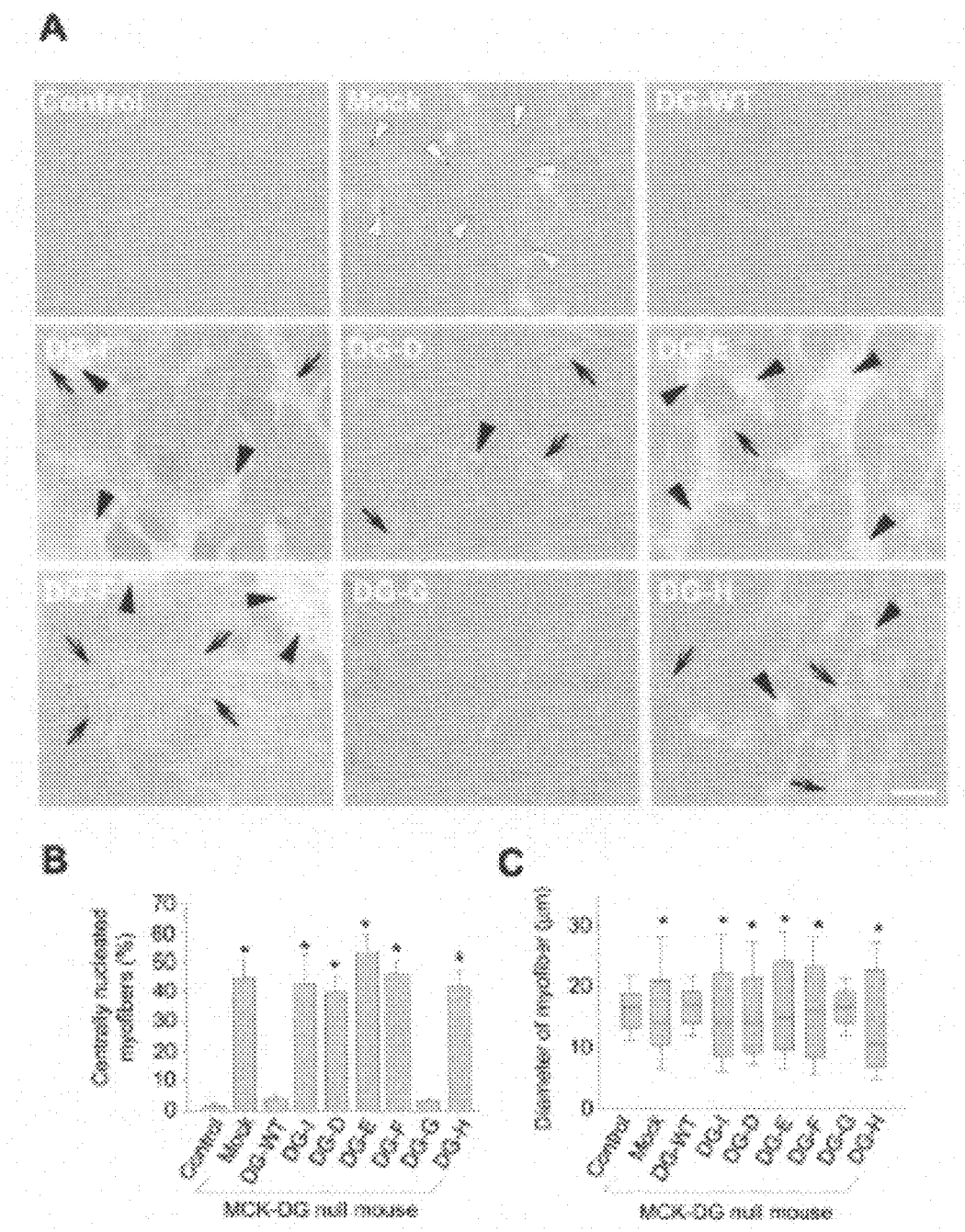
FIG. 12 shows a histological analysis of MCK-DG null muscles after expression of DG deletion mutant proteins. Laminin-binding activity is essential to maintain muscle cell integrity. A) The pathological phenotype after expression of deletion mutants of DG in vivo was examined by hematoxylin-eosin staining. Numerous regenerating fibers with central nuclei are seen in MCK-DG null mice with mock injection (open arrowhead). In the muscles expressing DG-I, DG-D, DG-E, DG-F, or DG-H, fibrous connective tissue is increased (arrow) and fatty infiltration is detected (closed arrowhead). In sharp contrast, the muscles expressing DG-WT and DG-G are fully rescued from dystrophic pathology. B) The percentage of myofibers with centrally located nuclei in the MCK-DG null mice expressing DG-WT and DG-G was not statistically different from the control mice. C) The variability of myofiber diameter in the MCK-DG null mice expressing DG-WT and DG-G was decreased and not statistically different from the control mice. The bar in the box represents the mean diameter. The boxes indicate the 25 and 75 percentile values and the error bars represent the 10 and 90 percentile values.
Figure 13:
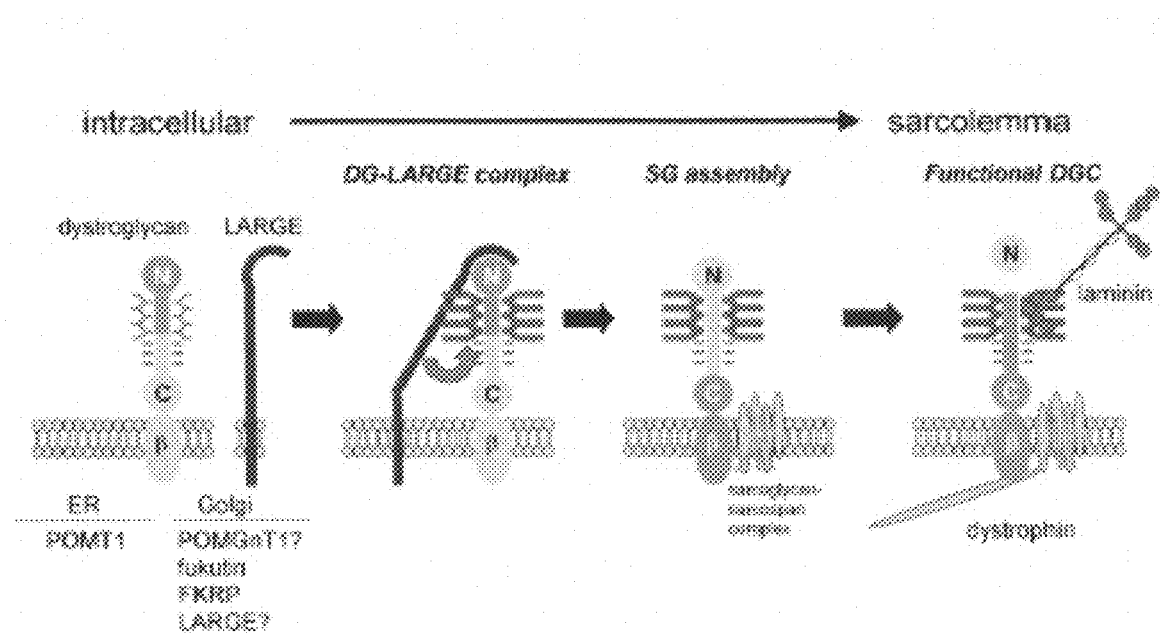
FIG. 13 illustrates a multi-step molecular pathway for the functional expression of DG. Distinct domains are responsible for each step of post-translational modification of DG. Important domains in each step are represented in dark red. The N-terminal domain and the first-half of the mucin-like domain are necessary for the functional glycosylation. The N-terminal domain is recognized by LARGE. LARGE-dependent modification takes place within the first-half of the mucin-like domain. The C-terminal domain and/or β-DG are responsible for the sarcoglycan assembly. All steps are necessary for the functional expression of DG to maintain muscle cell integrity and basement membrane assembly.

Surprisingly, hematoxylin-eosin staining revealed that expression of DG-I, DG-D, DG-E, DG-F or DG-H exacerbated the dystrophic phenotype of the mutant mice in spite of full restoration of the DGC (FIG. 12). The pathological phenotype of the MCK-DG null mouse includes numerous regenerating fibers in skeletal muscle with no evidence of tissue fibrosis and/or fatty infiltration (Cohn et al., 2002). However, after expression of DG-D, DG-E, DG-F or DG-H, fibrosis and fatty infiltration was commonly observed (FIG. 12A). In contrast, expression of DG-WT or DG-G proteins that bind to laminin, completely rescued the mouse from dystrophic pathology (FIG. 12A). Quantitative morphometric analyses were performed by recording the percentage of fibers with centrally located nuclei, and fiber diameter variability, which reflect ongoing muscle regeneration and are both increased in muscular dystrophy. MCK-DG null mice injected with saline (Mock), or expressing DG-I, DG-D, DG-E, DG-F or DG-H had a significantly higher percentage of fibers with central nuclei and fiber diameter variability than control Cre-negative mice. The expression of DG-WT or DG-G in mutant mice prevented the increase in central nucleation and fiber diameter variability (FIGS. 12B and C). Taken together, these results provide in vivo evidence that the DGC assembly mediated by β-DG with the C-terminal domain of α-DG is not sufficient, and that the α-DG-laminin interaction is crucial to prevent muscle cell degeneration. These results demonstrate that the molecular recognition of α-DG by LARGE through the N-terminal domain of α-DG is essential for the subsequent functional glycosylation that underlies the pathology of several forms of muscular dystrophy.

Experimental Procedures

Antibodies

Antibodies to α-DG (IIH6, FPD, and GT20ADG), and β-DG were described previously (Ervasti et al., 1993; Ibraghimov-Beskrovnaya et al., 1992; Michele et al., 2002). Antibodies against α-sarcoglycan, δ-sarcoglycan, sarcospan, dystrophin and β-sarcoglycan were described elsewhere (Duclos et al., 1998b). Antibodies against LARGE and α-DG N-terminal fragment (rabbit 73) were raised in rabbits. Synthetic peptides corresponding to the C-terminal sequence of mouse LARGE (C-YGFAALKYLTAENN; SEQ ID NO: 16) and the N-terminal sequence of rabbit DG (HWPSEPSEAVRDWEN; SEQ ID NO: 17) were used as antigens, respectively. Specificity of anti-LARGE antibody was confirmed by Western blotting using TSA201 cell lysates prepared before and after LARGE overexpression. Monoclonal antibody against γ-sarcoglycan, 21B5, was generated in collaboration with Dr. Louise Anderson. Anti-laminin and anti-heparan sulfate proteoglycan (perlecan) antibodies were purchased from Sigma and Chemicon International Inc, respectively. Antibodies against laminin α2-chain, laminin α1-chain and α1 syntrophin were kind gifts from Drs. Peter Yurchenco, Lydia Sorokin and Stanley Froehner, respectively. Peroxidase conjugated secondary antibodies were obtained from Roche. Biotinylated anti-human IgG was from Vector. Cy3 and FITC conjugated secondary antibodies were from Jackson Immuno Research. Peroxidase conjugated avidin was from Pierce.

Expression and Purification of Recombinant α-DG-IgG Fc Fusion Proteins

Construction of α-DG-IgG Fc fusion proteins were described elsewhere (Kunz et al., 2001). Construction of DGFc6 is shown in the Supplement materials. TSA201 cells were grown in Dulbecco's modified eagle media (DMEM) supplemented with 10% fetal bovine serum (FBS), 2 mM L-glutamine and penicillin-streptomycin (GIBCO-BRL). Cells were transiently transfected using FuGene 6 (Roche). The conditioned medium and the cells were collected 4 days after transfection unless stated otherwise. For CMK-treatment, after the transfection, cells were cultured in the presence of 20 μM CMK (ALEXIS) for 2-4 days. The cells were lysed in Buffer A (50 mM Tris-HCl, pH 7.4, 150 mM NaCl, 1% Triton X-100, 0.6 μg/ml of pepstatin A, 0.5 μg/ml of aprotinin, 0.5 μg/ml of leupeptin, 0.75 mM of benzamidine, 0.1 mM of PMSF, 0.4 μg/ml of calpain inhibitor and 0.4 μg/ml of calpeptin) for 2 h at 4° C. and the extracts were collected by centrifugation at 20,000×g for 10 min. The cell extracts and conditioned medium were incubated with protein A-agarose (Santa Cruz) overnight at 4° C. The beads were washed extensively with Buffer A and the bound DGFc proteins were eluted by 100 mM glycine-HCl, pH 2.8, or by boiling in LSB.

Deglycosylation Experiments

Thirty μl of purified DGFc5 preparations were boiled for 5 min in the presence of 0.7% SDS, then Triton X-100 was added to a final concentration of 1% and pH was adjusted to 5.5 by adding 50 mM sodium acetate. The mixture was incubated with 100 mU of Vibrio cholerae neuraminidase (Roche) and 2 mU of O-glycosidase (Roche) at 37° C. for 16 h. The pH was neutralized by adding 100 mM sodium phosphate buffer and the mixture was then incubated with 10 mU of N-glycosidase (Glyko) at 37° C. for 16 h. Chemical deglycosylation was performed as previously described (Ervasti et al., 1993).

LARGE Expression

Generation of E1-deficient recombinant adenovirus Ad5 LARGE/eGFP was described elsewhere (Barresi, et al., 2004). TSA201 cell cultures were infected with viral vector for 2 h with multiplicity of infection (MOI) of 10 in DMEM supplemented with 2% FBS and then the culture medium was changed to 10% FBS-containing DMEM. Cell lysates were prepared after 2 days post-infection as described above. For detection of DGFc-LARGE interaction, LARGE-expressed cell lysates were incubated with DGFc-protein A-beads at 4° C. for 3 h. After extensive washing with buffer containing 50 mM Tris-HCl (pH 7.4), 150 mM NaCl, and 0.1% Triton X-100, bound materials were eluted with LSB.

Adenovirus Mediated Gene Transfer into ES Cell

Generation of replication-deficient adenoviral (AdV) vectors and α-DG deletion constructs were described elsewhere (Kunz et al., 2001). $DG^{+/-}$ clone (354.C3) and $DG^{-/-}$ clone (354.B11) of ES cells were cultured as previously described (Henry and Campbell, 1998). ES cells were infected by AdV constructs with MOI of 3 in DMEM supplemented with 2% FBS overnight. Next day, the cells were processed for a laminin and perlecan clustering assay as described elsewhere (Henry et al., 2001). For biochemical analysis, the cells were harvested 48 h after infection and lysed with buffer A. After centrifugation, the supernatants were incubated with Jacalin-agarose (Vector) overnight at 4° C. The beads were washed 3 times with buffer A and bound proteins were eluted by LSB.

Adenovirus Mediated Gene Transfer into Mouse Skeletal Muscle

One week old MCK-DG null mice and T30 L/L mice as control animals were injected percutaneously with $3×10^9$ particles in 10 μl of saline solution into the hamstrings. As mock injections, only the saline without viruses was injected. Five weeks after injection, the muscles were harvested for histological and immunofluorescence analysis.

Histological Analysis

Hematoxylin-eosin staining was performed as described elsewhere (Cohn et al., 2002). For the calculation of the percentage of myofibers with centrally located nuclei, 700 to 1200 myofibers from 5 different visual fields were observed and centrally nucleated fibers were counted. To assess the variability of myofiber diameter, the shortest diameter was measured in 250 myofibers. The statistical difference was evaluated using t-test.

Miscellaneous

Native α-DG was purified from rabbit skeletal muscle as described previously (Rambukkana et al., 1998). Western blotting, immunofluorescence analysis, ligand overlay, and solid-phase binding assays were described previously (Michele et al., 2002).

Construction of DGFc6

The DGFc6 construct was engineered as follows: using the DGFc5 construct (DGFc5 pcDNA3) as a template, the following primers were used to generate PCR fragments of α-DG (T7; 5'-GTAATACGACTCACTATAGGG-3' (SEQ ID NO: 18), DGSSR; 5'-TTCTCGAGTTTCGCGACTGAGC-CACGGCCACACAGA-3' (SEQ ID NO: 19), DGmucin; 5'-AAGGCGCCACACCCACACCTGTCAC-3' (SEQ ID NO: 20), DGXhoI; 5'-CACCTCGAGTCCGAGTGGTG-3' (SEQ ID NO: 21)). A T7-DGSSR PCR fragment (digested with KpnI and NruI, encoding the signal sequence of DG) and a DGmucin-DGXhoI PCR fragment (digested with SfoI and XhoI, encoding the mucin-like domain and the first half of C-terminal domains) were ligated along the XhoI fragment from DGFc5 pcDNA3 (encoding the second half of C-terminal domain and the Fc portion).

Binding of Extracellular Matrix Ligands to the N-Terminal Half of DGFc Proteins

Western blot and ligand overlay assays were performed on DGFc5, 4, 3 and 1 prepared from conditioned media. IIH6, laminin-1, laminin-2, and agrin bind only to the higher molecular weight purified protein product of DGFc5, 4 and 3, each of which contain the first-half of mucin-like domain, but do not bind to DGFc1, which lacks the mucin-like domain.

Proteolytical Processing of α-DG

A) Convertase-like activity cleaves α-DG. Cell culture in the presence of CMK protects degradation of the secreted form of DGFc5. Furin belongs to a proprotein convertase family and is inhibited by CMK. After the in vitro furin-treatment of the DGFc5 preparation from CMK-treated cell culture media, the 150 kDa band disappeared and CB staining intensity in the 120 kDa bands was increased. For the in vitro furin-treatment, DGFc5 preparations from CMK-treated cells were incubated with 5 U of furin (ALEXIS) in the buffer containing 100 mM HEPES-Tris (pH 7.4), 100 mM NaCl, 1 mM $CaCl_2$, 0.5% Triton X-100 at 37° C. for 2 h. B). The secreted form of DGFc5 lacks the N-terminal domain. Results of Edman analysis of CB stained DGFc5 proteins show that an amino acid sequence of Gln-Ile-His-Ala was obtained from a band at approximately 120 kDa in the DGFc5 preparation from conditioned medium without CMK treatment. This sequence corresponds to amino acid residues 313-316 of α-DG, immediately preceding the mucin-like domain. The N-terminal amino acid sequence of the 150 kDa band in the DGFc5 preparation from conditioned medium with CMK-treatment corresponds to the sequence starting from amino acid 30 in α-DG. N-terminal analysis of the 120 kDa band, which was increased after the in vitro furin-treatment, revealed that a convertase-like activity cleaved α-DG between $Arg^{312}$ and $Gln^{313}$.

Example 3

Identification of Acceptor Motif for LARGE-Dependent Glycosylation

Figure 14:
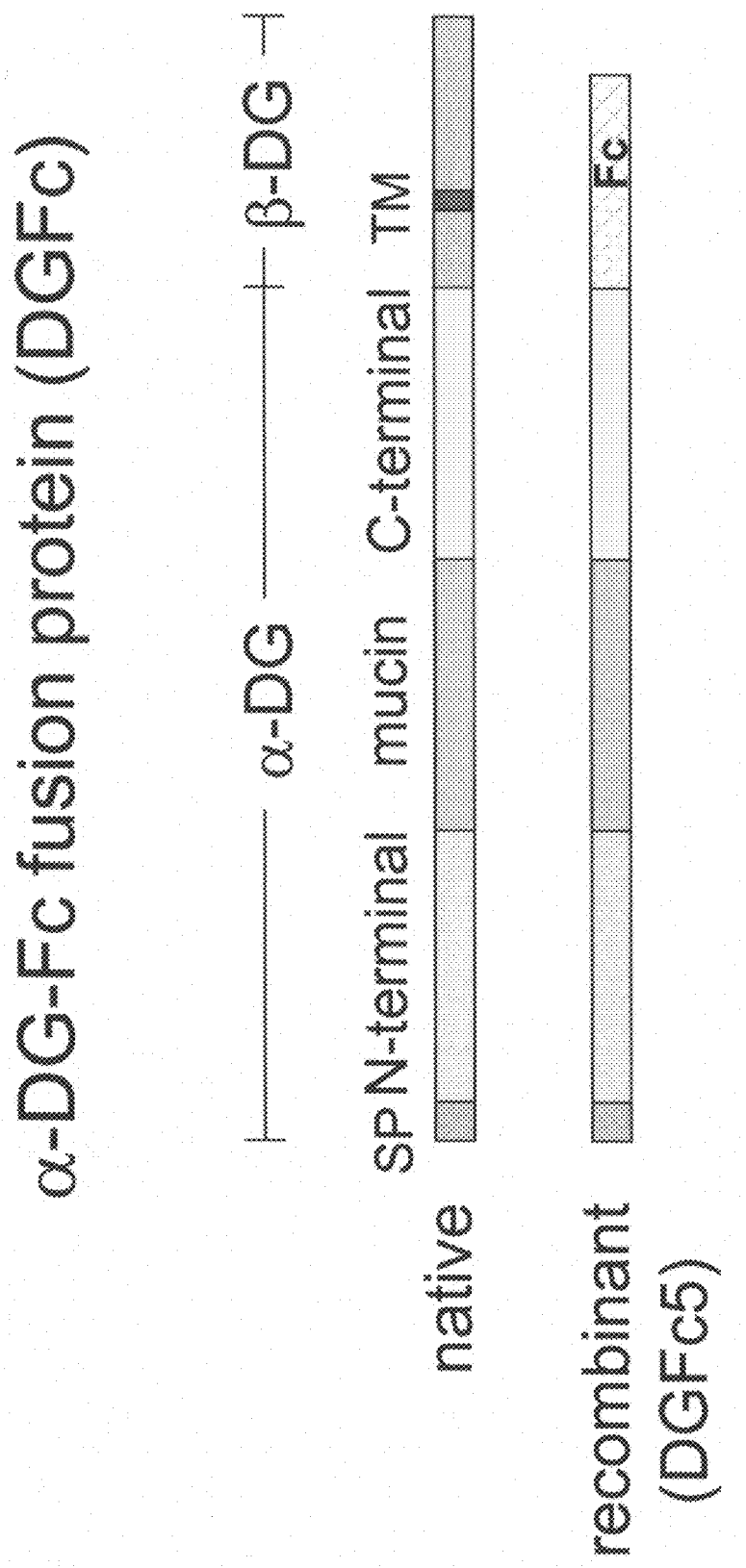
FIG. 14 shows a schematic of native α-DG (α-dystroglycan) and an α-DG-Fc fusion protein.

Results

α-DG consists of the N-terminal, mucin-like, and C-terminal domains (FIG. 14). The presence of the N-terminal domain is necessary for the functional glycosylation on the mucin-like domain (Kanagawa et al., 2004). Overexpression of LARGE induces hyperglycosylation of α-DG and strongly enhances ligand-binding activities of α-DG (Barresi et al., 2004). Importantly, the LARGE-dependent hyperglycosylation takes place in dystroglycanopathy cells lacking POMT1, POMGnT, and fukutin. Therefore, a novel therapeutic approach using LARGE toward to congenital muscular dystrophies was proposed. In order to determine the LARGE-dependent glycosylation region in the mucin-like domain, we generated various deletion mutants in the mucin-like domain as a fusion protein with Fc. Since the presence of the N-terminal domain is essential for successful glycosylation, all constructs contain the N-terminal domain. The N-terminal domain is processed off during protein secretion, therefore the final products do not contain the N-terminal domain (Kanagawa et al., 2004).

Figure 15:
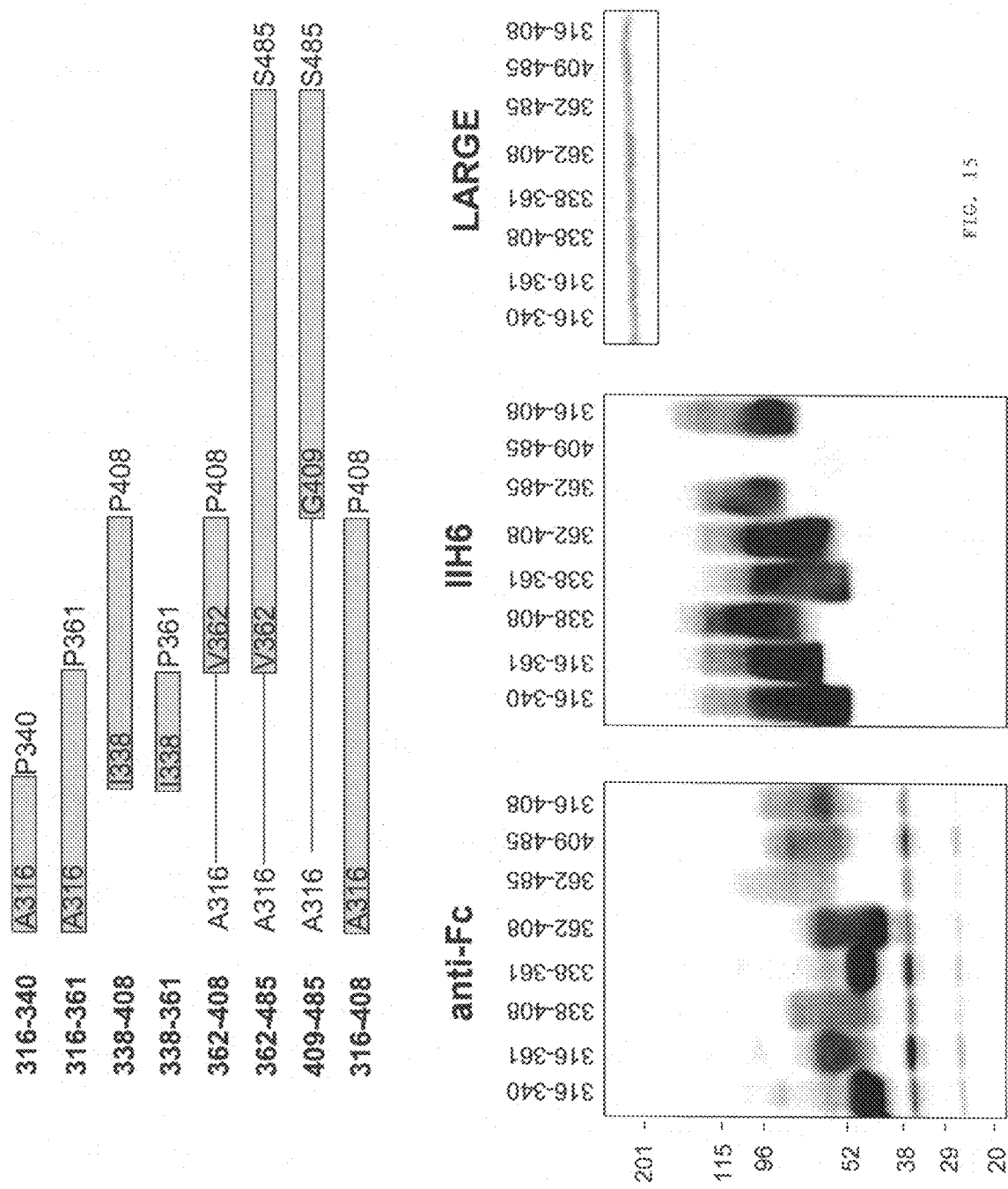
FIG. 15 shows a schematic of the α-DG deletion mutants used in Example 3. The results shown indicate that the presence of three independent regions could be modified by LARGE, 316-340, 338-361, and 362-408.

The deletion constructs were transfected to TSA201 cells with LARGE-expression vector. Two days after the co-transfection, DGFc proteins were purified from conditioned media, and analyzed for the functional glycosylation by Western blotting with 11H6. IIH6 is a monoclonal antibody to α-DG which recognizes only functionally glycosylated form. Anti-Fc and anti-LARGE antibodies were used for showing comparable amount of protein expression. The results indicate that the presence of three independent regions could be modified by LARGE, 316-340, 338-361, and 362-408 (FIG. 15). By comparing their amino acid sequence, we propose TPT(X)$_{3-4}$I(X)$_{1-2}$PT (SEQ ID NO: 4) is an acceptor motif for LARGE-dependent glycosylation (FIG. 16).

Materials and Methods

Construction of Expression Vectors

All DGFc constructs were generated by PCR-based method. For PCR amplification of deletion in the mucin-like domain following template and primers used as shown in appendix 1. The PCR products were digested with KpnI/BclI and ligated into KpnI/BamHI site of FcpcDNA3 (Kunz et al., 2001). For the construction of 338-408, two fragments were amplified from DGFc5pcDNA3 (Kunz et al., 2001) with T7×315R and 338F×408R. The PCR products were ligated using blunt-end PmlI EcoRV, and then ligated into FcpcDNA3. For the construction of 362-485, two fragments were amplified from DGFc5pcDNA3 with T7×362.485R and 362.485F×485R. The PCR products were mixed, extended with T7×485R, and then ligated into FcpcDNA3. For the construction of 409-485, two fragments were amplified from DGFc5pcDNA3 with T7×409.485R and 409.485F×485R. The PCR products were mixed, extended with T7×485R, and then ligated into FcpcDNA3.

For the LARGE expression vector, SmaI/NheI fragments from human LARGE cDNA (Barresi et al., 2004) was ligated into EcoRV/NheI sites of pIRESpuro3.

Expression and Purification of DGFc Proteins

TSA201 cells were grown in Dulbecco's modified eagle media (DMEM) supplemented with 10% fetal bovine serum (FBS), 2 mM L-glutamine and penicillin-streptomycin (GIBCO-BRL). Cells were transiently transfected using FuGene 6 (Roche). The conditioned medium and the cells were collected 2 days after transfection unless stated otherwise. The cells were lysed in Buffer A (50 mM Tris-HCl, pH 7.4, 150 mM NaCl, 1% Triton X-100, 0.6 µg/ml of pepstatin A, 0.5 µg/ml of aprotinin, 0.5 µg/ml of leupeptin, 0.75 mM of benzamidine, 0.1 mM of PMSF, 0.4 µg/ml of calpain inhibitor and 0.4 µg/ml of calpeptin) for 2 h at 4° C. and the extracts were collected by centrifugation at 20,000×g, for 10 mim. The cell extracts and conditioned medium were incubated with protein A-agarose (Santa Cruz) overnight at 4° C. The beads were washed extensively with Buffer A and the bound DGFc proteins were eluted by 100 mM glycine-HCl, pH 2.8, or by boiling in Laemmli sample buffer (LSB).

The invention claimed is:

1. A method for increasing the ligand binding activity of α-dystroglycan in a muscle cell in a subject in need of increased ligand binding activity of α-dystroglycan in the muscle cell, the method comprising administering intramuscularly to the skeletal muscle of the subject a composition comprising human LARGE effective to increase ligand binding activity of α-dystroglycan in the muscle cell of the subject, wherein the subject is mouse or human.

2. The method of claim 1 wherein increasing the ligand binding activity of α-dystroglycan comprises increasing the functional glycosylation of α-dystroglycan.

3. The method of claim 1 wherein the composition is effective to increase glycosyltransferase activity in a muscle cell in the subject.

4. The method of claim 1 wherein increasing the ligand binding activity of α-dystroglycan at least partially prevents or treats muscle degeneration and wherein the muscle degeneration is caused by MDC1D.

5. The method of claim 4 wherein muscle degeneration is due to a condition selected from the group consisting of an injury-related weakness, muscle atrophy, and an age-related weakness.

6. The method of claim 1 wherein the composition comprises an exogenous construct effective to increase glycosyltransferase activity.

7. The method of claim 1 wherein the composition is effective to increase endogenous glycosyltransferase activity.

8. The method of claim 2, wherein the glycosylation involves O-mannosyl glycosylation.

9. The method of claim 4 wherein muscle degeneration has arisen from a congenital or genetically predisposed muscular dystrophy.

10. A method of increasing the ligand binding activity of α-dystroglycan by stimulating glycosylation of α-dystroglycan in a muscle cell, comprising:
   a) providing: i) a muscle cell comprising α-dystroglycan from a murine or human subject in need of increased ligand binding activity of α-dystroglycan in the muscle cell, ii) a composition effective in increasing the ligand binding activity of α-dystroglycan by stimulating glycosylation of α-dystroglycan, said composition comprising human LARGE; and,
   b) contacting said muscle cell comprising α-dystroglycan with said composition effective in increasing the ligand binding activity of α-dystroglycan by stimulating glycosylation of α-dystroglycan under conditions and for a period of time sufficient to increase glycosylation of α-dystroglycan.

11. The method of claim 10, wherein said cell comprising of α-dystroglycan is contacted with said composition effective in stimulating glycosylation under conditions and for a period of time sufficient to increase functional glycosylation of α-dystroglycan in vitro.

12. The method of claim 10, wherein said cell comprising of α-dystroglycan is contacted with said composition effective in stimulating glycosylation under conditions and for a period of time sufficient to increase functional glycosylation of α-dystroglycan in vivo.

* * * * *

```
                        SEQUENCE LISTING

<160> NUMBER OF SEQ ID NOS: 21

<210> SEQ ID NO 1
<211> LENGTH: 25
<212> TYPE: PRT
<213> ORGANISM: Homo sapiens

<400> SEQUENCE: 1

Ala Thr Pro Thr Pro Val Thr Ala Ile Gly Pro Pro Thr Thr Ala Ile
  1               5                  10                  15

Gln Glu Pro Pro Ser Arg Ile Val Pro
            20                  25

<210> SEQ ID NO 2
<211> LENGTH: 24
<212> TYPE: PRT
<213> ORGANISM: Homo sapiens

<400> SEQUENCE: 2

Ile Val Pro Thr Pro Thr Ser Pro Ala Ile Ala Pro Pro Thr Glu Thr
  1               5                  10                  15

Met Ala Pro Pro Val Arg Asp Pro
            20

<210> SEQ ID NO 3
<211> LENGTH: 47
<212> TYPE: PRT
<213> ORGANISM: Homo sapiens

<400> SEQUENCE: 3

Val Pro Gly Lys Pro Thr Val Thr Ile Arg Thr Arg Gly Ala Ile Ile
  1               5                  10                  15

Gln Thr Pro Thr Leu Gly Pro Ile Gln Pro Thr Arg Val Ser Glu Ala
```

```
                    20                  25                  30
Gly Thr Thr Val Pro Gly Gln Ile Arg Pro Thr Leu Thr Ile Pro
        35                  40                  45

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(7)
<223> OTHER INFORMATION: Variable amino acid and this region may
      encompass 3 or 4 residues
<220> FEATURE:
<221> NAME/KEY: MOD_RES
<222> LOCATION: (9)..(10)
<223> OTHER INFORMATION: Variable amino acid and this region may
      encompass 1 or 2 residues

<400> SEQUENCE: 4

Thr Pro Thr Xaa Xaa Xaa Xaa Ile Xaa Xaa Pro Thr
 1               5                  10

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttgatcagg cacgatcctg gacggcgg                                       28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tttgatcagg atccctgact ggaggagc                                       28

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttcacgtgga tctgccttcg gatacgc                                        27

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aatcgcgaat cgtgcctacc cccacttct                                      29
```

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tttgatcagg aatggtcacc gttgcacg                                        28

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgtgggctt cccaggaaca ggggcatgga tctgccttcg gatac                     45

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtatccgaag gcagatccat gcccctgttc ctgggaagcc cacgg                     45

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttgatcact ggtggtggtg cggatacga                                       29

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgctgtggg ctccacgtag ccggcatgga tctgccttcg gatac                     45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtatccgaag gcagatccat gccggctacg tggagcccac agcag                     45

```
<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Val Lys Arg
  1

<210> SEQ ID NO 16
<211> LENGTH: 14
<212> TYPE: PRT
<213> ORGANISM: Mus musculus

<400> SEQUENCE: 16

Tyr Gly Phe Ala Ala Leu Lys Tyr Leu Thr Ala Glu Asn Asn
  1               5                  10

<210> SEQ ID NO 17
<211> LENGTH: 15
<212> TYPE: PRT
<213> ORGANISM: Oryctolagus cuniculus

<400> SEQUENCE: 17

His Trp Pro Ser Glu Pro Ser Glu Ala Val Arg Asp Trp Glu Asn
  1               5                  10                  15

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtaatacgac tcactatagg g                                            21

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttctcgagtt tcgcgactga gccacggcca cacaga                            36

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaggcgccac acccacacct gtcac                                        25

<210> SEQ ID NO 21
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 21
cacctcgagt ccgagtggtg                                                    20
```